US012697424B2

(12) United States Patent
Maheshwari et al.

(10) Patent No.: US 12,697,424 B2
(45) Date of Patent: Aug. 4, 2026

(54) PERSONALIZED PERITONEAL DIALYSIS TREATMENT USING DESIGN OF EXPERIMENT TECHNIQUES

(71) Applicants: Fresenius Medical Care Holdings, Inc., Waltham, MA (US); Fresenius Medical Care Deutschland, GMBH, Bad Homburg (DE)

(72) Inventors: Vaibhav Maheshwari, Natick, MA (US); Paul Chamney, Tring-Herts (GB); Bernd Eberle, Herschweiler-Pettersheim (DE)

(73) Assignees: Fresenius Medical Care Holdings, Inc., Waltham, MA (US); Fresenius Medical Care Deutschland, GMBH, Bad Homburg (DE)

( * ) Notice: Subject to any disclaimer, the term of this patent is extended or adjusted under 35 U.S.C. 154(b) by 449 days.

(21) Appl. No.: 18/088,031

(22) Filed: Dec. 23, 2022

(65) Prior Publication Data

US 2023/0211058 A1 Jul. 6, 2023

Related U.S. Application Data

(60) Provisional application No. 63/295,211, filed on Dec. 30, 2021.

(51) Int. Cl.
*A61M 1/16* (2006.01)
*G16H 10/60* (2018.01)
*G16H 20/40* (2018.01)
(52) U.S. Cl.
CPC .......... *A61M 1/1613* (2014.02); *G16H 10/60* (2018.01); *G16H 20/40* (2018.01); *A61M 2205/3327* (2013.01); *A61M 2205/52* (2013.01)

(58) Field of Classification Search
None
See application file for complete search history.

(56) References Cited

U.S. PATENT DOCUMENTS

| 2018/0043075 A1 * | 2/2018 | Gerber | ............... A61M 1/1609 |
| 2018/0043078 A1 * | 2/2018 | Gerber | ............... A61M 1/1613 |

(Continued)

FOREIGN PATENT DOCUMENTS

| WO | WO-2010135078 A2 * | 11/2010 | .......... A61M 1/1611 |

OTHER PUBLICATIONS

Stelin et al., "A phenomenological interpretation of the variation in dialysate volume with dwell time in CAPD," Kidney International, vol. 38 (1990) pp. 465-472.

(Continued)

*Primary Examiner* — Jonathan M Peo
(74) *Attorney, Agent, or Firm* — KDW Firm PLLC

(57) ABSTRACT

The described technology generally includes systems and processes for a PD optimization process may operate to estimate, predict, or otherwise determine the value of PD dose variables values based on patient characteristics and/or PD prescription information. In one embodiment, a PD optimization process may be or may include a UFV determination process, operative to determine a predicted UFV for a patient. In some embodiments, the UFV determination process may include training a computational model to generate a predicted UFV output based on input of patient characteristics, PD prescription information, PD outcomes (for instance, UFV), and/or historical information associated with patient characteristics, PD prescription information, and/or PD outcomes. In some embodiments, a feedback control process with continuous Intraperitoneal Pressure (IPP) and hydration status measurements may be used to (Continued)

keep the hydration status of the patient within a target level ran. Other embodiments are described.

20 Claims, 31 Drawing Sheets

(56) References Cited

U.S. PATENT DOCUMENTS

| | | | |
|---|---|---|---|
| 2018/0117234 A1 | 5/2018 | Neftel | |
| 2018/0361048 A1* | 12/2018 | Scarpaci | ............. A61M 1/1664 |
| 2022/0347363 A1 | 11/2022 | Vartia | |

OTHER PUBLICATIONS

Amici, G. "Mathematical models for prescription and delivery in peritoneal dialysis." Nephrology, dialysis, transplantation : official publication of the European Dialysis and Transplant Association— European Renal Association vol. 13 Suppl 6 (1998): 120-4.
International Search Report and Written Opinion for the International Application No. PCT/US2022/053930, mailed Jul. 13, 2023, 22 pages.
International Search Report and Written Opinion in International Application No. PCT/EP2022/087988, mailed on Jun. 2, 2023, 23 pages.
International Preliminary Report on Patentability for International Application No. PCT/US2022/053930, mailed on Jul. 11, 2024, 12 pages.

* cited by examiner

PERSONALIZED PERITONEAL DIALYSIS TREATMENT USING DESIGN OF EXPERIMENT TECHNIQUES

CROSS-REFERENCE TO RELATED APPLICATIONS

This application claims the benefit to U.S. Provisional Application No. 63/295,211, filed Dec. 30, 2021, and is related to co-owned U.S. Provisional Application No. 63/295,203, filed Dec. 30, 2021, the entire contents of which are incorporated herein by reference in their entirety.

FIELD

The disclosure generally relates to processes for managing fluid status in patients receiving peritoneal dialysis (PD), and, more particularly, to techniques for predicting the ultrafiltration volume (UFV) of a PD cycle.

BACKGROUND

In general, a cycle of PD treatment includes the steps of filling the peritoneal cavity of the abdomen with dialysate, allowing the dialysate to dwell in the peritoneal cavity for a predetermined period (i.e., a dwell time), then draining the PD effluent (or spent dialysate) from the peritoneal cavity. The peritoneal membrane serves as a natural dialyzer and toxic uremic waste metabolites and various ions diffuse from the patient's bloodstream across the membrane into the dialysate due to concentration gradients. At the same time, fluid is drawn into the peritoneal cavity by an osmotic gradient. The PD effluent is drained (along with the toxins and other waste components), discarded, and replaced with fresh dialysis solution on a semi-continuous or continuous basis.

Maintaining fluid status in patients receiving peritoneal dialysis (PD) represents a major clinical challenge. This demands control of the fluid volume removed, the ultrafiltration volume (UFV), during each treatment cycle. In general, the UFV is a target volume of fluid to be removed each dialysis cycle in order to maintain a patient's target fluid status, for instance, the weight that would be achieved with normal kidney function. A PD prescription may be configured with a set of dosage parameters selected to achieve a target UFV. Non-limiting examples of parameters may include dwell time, dialysate composition (compound and concentration), and fill volume. However, conventional techniques are not able to efficiently or accurately determine a UFV for a patient based on known information, such as patient characteristics and PD parameters. Current processes attempt to determine a PD prescription based on trial-and-error processes which are inaccurate and incapable of providing adequate information. In addition, such manual processes are costly, time consuming, and require the patient to make repeat visits to the clinic.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one embodiment, an apparatus may include at least one processor and a memory coupled to the at least one processor. The memory may include instructions that, when executed by the at least one processor, may cause the at least one processor to access prescription information for a peritoneal dialysis (PD) process for a patient, and provide the prescription information as at least one input to at least one computational model to determine a predicted intraperitoneal volume (IPV), the at least one computational model trained to determine the predicted IPV based on the prescription information and patient information for at least one PD process cycle for the patient or a population of patients associated with the patient.

In some embodiments of the apparatus, the prescription information may include a fill volume, a dwell time, and osmotic agent information. In various embodiments of the apparatus, the patient information may include at least one of hydration status, activity level, and treatment time-of-day.

In some embodiments of the apparatus, the instructions, when executed by the at least one processor, may cause the at least one processor to provide the patient information as the at least one input to the at least one computational model to determine the predicted IPV.

In exemplary embodiments of the apparatus, the instructions, when executed by the at least one processor, may cause the at least one processor to receive a measured IPV during the PD treatment process for the patient, and determine an error value based on a difference between the predicted IPV and the measured IPV. In some embodiments of the apparatus, the instructions, when executed by the at least one processor, may cause the at least one processor to update a training of the at least one computational model using the error value.

In various embodiments of the apparatus, wherein the at least one computational model may be trained to determine a predicted ultrafiltration volume (UFV) based on the at least one input of the prescription information and a measured drain volume for the PD process.

In some embodiments of the apparatus, the instructions, when executed by the at least one processor, may cause the at least one processor to receive the measured drain volume for the PD process, and provide the measured drain volume and the prescription information to the at least one computational model to determine the predicted UFV.

In exemplary embodiments of the apparatus, the computational model may be configured to determine the predicted UFV according to the following regression model $UFV_{Pred}(t) = a + b \cdot [Glu] + c \cdot T_{dwell} + d \cdot [Glu]^2 + e \cdot [Glu] \cdot T_{dwell} + f \cdot T_{dwell}^2$, where a, b, c, d, e, and f are regression model coefficients specific to the patient.

In some embodiments of the apparatus, the instructions, when executed by the at least one processor, may cause the at least one processor to receive a measured UFV for the PD process, determine an error value based on a comparison of the predicted UFV and the measured UFV, and determine a health condition of the patient based on the error value. In various embodiments of the apparatus, the health condition comprising peritonitis.

In one embodiment, an apparatus may include at least one processor and a memory coupled to the at least one processor. The memory may include instructions that, when executed by the at least one processor, may cause the at least one processor to receive prescription dosage information for a peritoneal dialysis (PD) process for a patient, determine a predicted ultrafiltration volume (UFV) for the patient by processing the prescription information via a trained computational model, the trained computational model trained based on at least one PD process cycle of the patient and a corresponding ultrafiltration volume measurement, and determine a treatment recommendation for the patient based on the fluid status information.

In some embodiments of the apparatus, the prescription dosage information may include a fill volume, a dwell time, and osmotic agent information.

In various embodiments of the apparatus, the instructions, when executed by the at least one processor, may cause the at least one processor to receive patient information, and determine the predicted UFV using the computational model based on the patient information and the prescription information. In some embodiments of the apparatus, the patient information may include at least one of time of day, activity level, or fluid intake.

In various embodiments of the apparatus, the instructions, when executed by the at least one processor, may cause the at least one processor to receive a measured UFV for the PD process, determine an error value based on a comparison of the predicted UFV and the measured UFV, and determine a health condition of the patient based on the error value.

In one embodiment, a method may include receiving prescription dosage information for a peritoneal dialysis (PD) process for a patient; and determining a predicted ultrafiltration volume (UFV) for the patient by processing the prescription information via a trained computational model, the trained computational model trained based on at least one PD process cycle of the patient and a corresponding ultrafiltration volume measurement.

In some embodiments of the method, the method may include determining a treatment recommendation for the patient based on the fluid status information. In various embodiments of the method, the method may include performing a PD treatment on the patient based on the UFV prediction. In some embodiments of the method, the prescription dosage information may include a fill volume, a dwell time, and osmotic agent information.

BRIEF DESCRIPTION OF THE DRAWINGS

By way of example, specific embodiments of the disclosed machine will now be described, with reference to the accompanying drawings, in which:

FIG. 26 illustrates a computing architecture in accordance with the present disclosure;

DETAILED DESCRIPTION

Figure 1A:
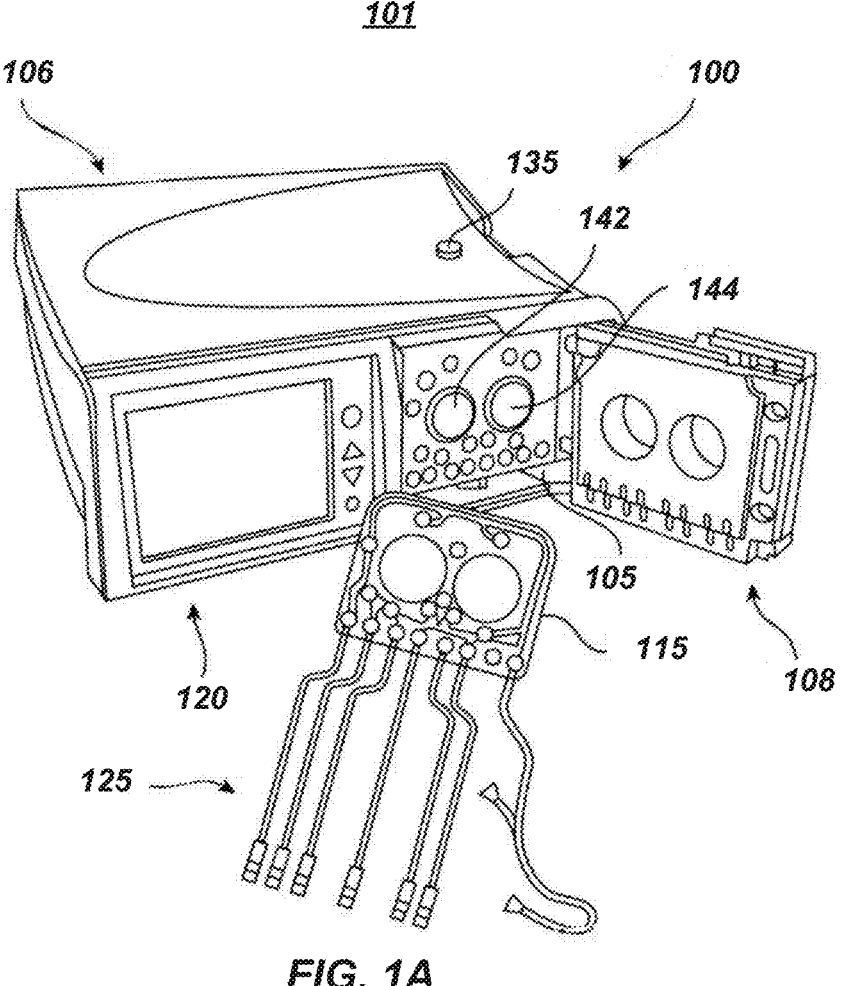
FIGS. 1A and 1B illustrate an exemplary PD system in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and more fully convey the scope of the subject matter to those skilled in the art. In the drawings, like numbers refer to like elements throughout.

Maintaining fluid balance in patients receiving peritoneal dialysis (PD) treatment is a central goal of adequate PD therapy. Using conventional methods, if a suboptimal fluid status is identified either by patient symptoms or through other clinical examination, the PD prescription must be revised to correct the patient's fluid status. This may be achieved by manipulating the fluid removed due to PD by different treatment prescriptions. Fluid removal by PD may be referred to as ultrafiltration (UF).

Ultrafiltration is achieved by introducing an osmotic agent (for example, glucose, polyglucose, amino acids, and/or the like) into the PD fluid. The osmotic agent causes fluid to be drawn from the interstitial spaces into the peritoneal cavity.

Typically, during a PD dwell with glucose as osmotic agent, the intraperitoneal volume rises to a peak and then, due to the absorption of glucose across the peritoneal membrane, there is an associated decrease in the intraperitoneal volume. Thus, the timing of the drain phase is a very important determinant of the overall fluid removed from the patient and, therefore, the UFV. In determining a PD prescription, a challenge is to ascertain the right combination of dose variables (e.g., fill volume, dwell duration, glucose composition, and/or the like) that deliver a desired UFV (or UFV range). Furthermore, there are often several prescription options which can lead to the same UFV, for example, with different glucose loads to the patient. Using conventional methods, the optimization of the dose variables in a prescription is a trial-and-error process which is costly, time consuming, and requires the patient to make repeat visits with a healthcare professional, often at a treatment facility.

Once an optimal prescription has been identified, there is generally not a re-assessment of the patient (unless a serious health complication arises). Accordingly, there is a tendency to maintain the same prescription for as long as possible, which invariably leads to the practice of imposing rigid and fixed PD treatment regimens, even though they may be or may become suboptimal (and even damaging) to the patient. This dramatically limits any possibility for flexible treatment schedules that would better suit an individual patient's lifestyle and/or promote optimal health. Essentially, any changes in lifestyle or other factors such as declining renal function or progressive membrane failure warrant a change in the prescription. Weighed against this, however, frequent revisions of prescriptions may be too arduous in clinical practice.

Ultrafiltration failure (UFF) or lack of ultrafiltration is a major cause of dropout in PD. While alterations in the anatomical structure of the membrane are in large part responsible for reducing UF capacity, the effects can be mitigated by appropriate changes to the prescription. However, in most cases, conventional methods tend to increase the concentration of the osmotic agent (e.g., glucose) in the dialysate. This further increases glucose (or other osmotic agent) exposure to the membrane, which may be linked to accelerated membrane damage. Alternative options include changing the dwell period, but without objective information and/or tools to control the timing of the drain phase, this option is generally ineffective and/or is not investigated.

Accordingly, some embodiments may provide a PD optimization process. In various embodiments, a PD optimization process may operate to estimate, predict, or otherwise determine the value of PD dose variables based on patient characteristics and/or PD prescription information. In one embodiment, a PD optimization process may be or may include a UFV determination process, operative to determine a predicted UFV for a patient. In some embodiments, the UFV determination process may include training a computational model to generate a predicted UFV output based on input of patient characteristics, PD prescription information, PD outcomes (for instance, UFV), and/or historical information associated with patient characteristics, PD prescription information, and/or PD outcomes.

Computational model-based processes may be used to predict the UFV when supplied with prescription (dose) variables and other input information that can influence the accuracy of the UFV prediction. In some embodiments, the computational model-based processes may be trained, configured, or otherwise used with existing data that are available, underlining their applicability to different PD modalities (e.g., continuous ambulatory PD (CAPD), automated PD (APD)). The use of existing data from daily treatments, with only slight changes in the dose variables, can only result in a minimal model restricted to a narrow range in the vicinity of the current prescribed treatment conditions. In some embodiments, computational models may use designed experiments, for example, to facilitate a wider range of dose variable values.

In various embodiments, UFV determination processes may use a set of dose variables unique to an individual patient in the prediction of UFV. In some embodiments, the computational models may be provided with a continuous (or semi- or quasi-continuous) data stream, such that the individual patient dose variables can be continually refined. If patient circumstances change, for example, due to lifestyle changes, progressive peritoneal membrane impairment and/or the like, the model parameter sets can be adapted accordingly, thus providing long term tracking capability.

PD optimization processes may be used for various types of patients and/or use cases. For example, PD optimization processes may be used for small variations in routine PD prescriptions (a small-variation use case), a designed experiment use case (large-variation use case), and/or a rigid prescription use case, for example, use of a rigid prescription and/or a prescription given at a particular time of day, in which the same prescription is always (or substantially always) used. In the small-variation use case, the PD optimization process may operate to adapt its model parameters on any prescription that is assigned to a patient. In some embodiments, the PD optimization process (or UFV determination process) may operate to determine a UFV prediction with an accuracy within the range of prescription variation, provided to the associated computational model. In the designed experiment use case, PD prescriptions may be created that involve multiple discrete values of each dose variable. For example, for a minimum experiment, a choice of discrete values may include a minimum or maximum for each variable. Other types of experiments may also be generated. In addition, PD optimization processes may be used for various other types of use cases. Embodiments are not limited in this context.

Embodiments may use various types of computational models, processes, algorithms, statistical/empirical models, and/or the like. Non-limiting examples of computational models may include a machine learning (ML) model, an artificial intelligence (AI) model, a neural network (NN), an artificial neural network (ANN), a convolutional neural network (CNN), a deep learning (DL) network, a deep neural network (DNN), a recurrent neural network (RNNs), combinations thereof, variations thereof, and/or the like. Embodiments are not limited in this context.

One or more techniques described herein may enable increased adaptability, usability, and appeal of products, systems, and/or services offered via dialysis systems, particularly PD systems and computing systems used to generate prescriptions for patients for performing dialysis via a PD system, promoting improved products, systems, and/or services and leading to better functionality and increased convenience. In these and other ways, components/techniques described here may identify methods to increase efficiency, decrease user input, improve usability, and/or expand desirability via realization of optimized PD prescriptions, treatments, processes, configured equipment and/or computing devices, and/or the like in an accurate, reactive, efficient, dynamic, and scalable manner, resulting in several technical effects and advantages over conventional computer technology, including increased capabilities and improved adaptability. In various embodiments, one or more of the aspects, techniques, and/or components described herein may be implemented in a practical application via one or more computing devices, and thereby provide additional and useful functionality to the one or more computing devices, resulting in more capable, better functioning, and improved computing devices. Further, one or more of the aspects, techniques, and/or components described herein may be utilized to improve one or more technical fields including the PD treatment of patients, determination of health conditions (e.g., peritonitis), PD treatment research, and/or the like.

Figure 1B:
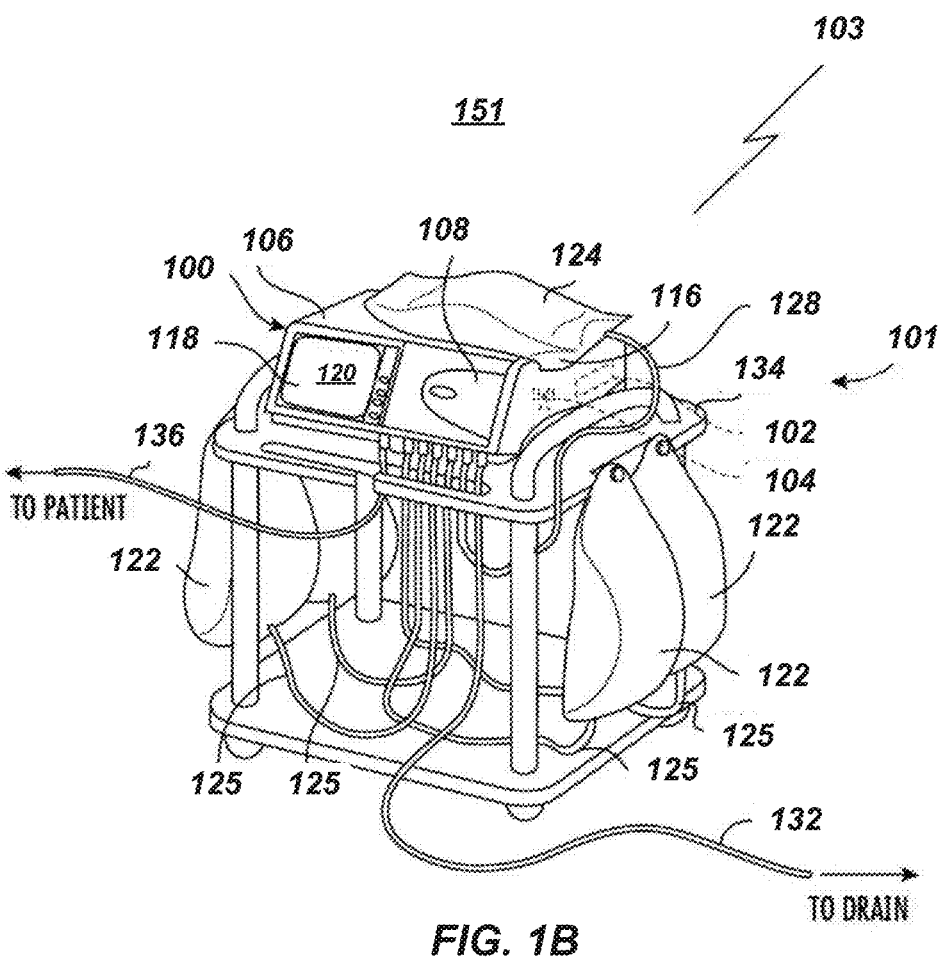

FIGS. 1A and 1B show an example of a peritoneal dialysis (PD) system 101, which is configured in accordance with an exemplary embodiment of the system described herein. In some implementations, the PD system 101 may be a home PD system, e.g., a PD system configured for use at a patient's home. The dialysis system 101 may include a dialysis machine 100 (e.g., a peritoneal dialysis machine 100, also referred to as a PD cycler) and in some embodiments the machine may be seated on a cart 134.

The dialysis machine 100 may include a housing 106, a door 108, and a cartridge interface including pump heads 142, 144 for contact with a disposable cassette, or cartridge 115, where the cartridge 115 is located within a compartment formed between the cartridge interface and the closed door 108 (e.g., cavity 105). Fluid lines 125 may be coupled to the cartridge 115 in a known manner, such as via a connector, and may further include valves for controlling fluid flow to and from fluid bags, including fresh dialysate and warming fluid. In another embodiment, at least a portion of the fluid lines 125 may be integral to the cartridge 115. Prior to operation, a user may open the door 108 to insert a fresh cartridge 115 and to remove the used cartridge 115 after operation.

The cartridge 115 may be placed in the cavity 105 of the machine 100 for operation. During operation, dialysate fluid may flow into a patient's abdomen via the cartridge 115, and spent dialysate, waste, and/or excess fluid may be removed from the patient's abdomen via the cartridge 115. The door 108 may be securely closed to the machine 100. Peritoneal dialysis for a patient may include a total treatment of approximately 10 to 30 liters of fluid, where approximately 2 liters of dialysate fluid are pumped into a patient's abdomen, held for a period of time, e.g., about an hour (the dwell duration), and then pumped out of the patient. This is repeated until the full treatment volume is achieved, and may, for example, occur overnight while a patient sleeps.

A heater tray 116 may be positioned on top of the housing 106. The heater tray 116 may be any size and shape to accommodate a bag of dialysate (e.g., a 5-liter (L) bag of dialysate) for batch heating. The dialysis machine 100 may also include a user interface such as a touch screen 118 and control panel 120 operable by a user (e.g., a caregiver or a patient) to allow, for example, set up, initiation, and/or termination of a dialysis treatment. In some embodiments, the heater tray 116 may include a heating element 135 for heating the dialysate prior to delivery into the patient.

Dialysate bags 122 may be suspended from hooks on the sides of the cart 134, and a heater bag 124 may be positioned on the heater tray 116. Hanging the dialysate bags 122 may improve air management as air content may be disposed by gravity to a top portion of the dialysate bag 122. Although four dialysate bags 122 are illustrated in FIG. 1B, any number "n" of dialysate bags may be connectable to the dialysis machine 100 (e.g., 1 to 5 bags, or more), and reference made to first and second bags does not limit the total number of bags used in a dialysis system 101. For example, the dialysis machine may have dialysate bags 122a, . . . 122n connectable in the system 101. In some embodiments, connectors and tubing ports may connect the dialysate bags 122 and lines for transferring dialysate. Dialysate from the dialysate bags 122 may be transferred to the heater bag 124 in batches. For example, a batch of dialysate may be transferred from the dialysate bags 122 to the heater bag 124, where the dialysate is heated by the heating element 135. When the batch of dialysate has reached a predetermined temperature (e.g., approximately 98°-100° F., 37° C.), the batch of dialysate may be flowed into the patient. The dialysate bags 122 and the heater bag 124 may be connected to the cartridge 115 via dialysate bag lines or tubing 125 and a heater bag line or tubing 128, respectively. The dialysate bag lines 125 may be used to pass dialysate from dialysate bags 122 to the cartridge 115 during use, and the heater bag line 128 may be used to pass dialysate back and forth between the cartridge and the heater bag 124 during use. In addition, a patient line 136 and a drain line 132 may be connected to the cartridge 115. The patient line 136 may be connected to a patient's abdomen via a catheter and may be used to pass dialysate back and forth between the cartridge and the patient's peritoneal cavity by the pump heads 142, 144 during use. The drain line 132 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 125), or fluid lines, via a cartridge. The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 100-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 118 and the control panel 120 may allow an operator to input various treatment parameters to the dialysis machine 100 and to otherwise control the dialysis machine 100. In addition, the touch screen 118 may serve as a display. The touch screen 118 may function to provide information to the patient and the operator of the dialysis system 101. For example, the touch screen 118 may display information related to a dialysis treatment to be applied to the patient, including information related to a prescription.

The dialysis machine 100 may include a processing module 102 that resides inside the dialysis machine 100, the processing module 102 being configured to communicate with the touch screen 118 and the control panel 120. The processing module 102 may be configured to receive data from the touch screen 118 the control panel 120 and sensors, e.g., weight, air, flow, temperature, and/or pressure sensors, and control the dialysis machine 100 based on the received data. For example, the processing module 102 may adjust the operating parameters of the dialysis machine 100.

The dialysis machine 100 may be configured to connect to a network 103. The connection to network 103 may be via a wired and/or wireless connection. The dialysis machine 100 may include a connection component 104 configured to facilitate the connection to the network 103. The connection component 104 may be a transceiver for wireless connections and/or other signal processor for processing signals transmitted and received over a wired connection. Other medical devices (e.g., other dialysis machines) or components may be configured to connect to the network 103 and communicate with the dialysis machine 100.

The user interface portion such as the touch screen 118 and/or control panel 120 may include one or more buttons for selecting and/or entering user information. The touch screen 118 and/or control panel 120 may be operatively connected to a controller (not shown) and disposed in the machine 100 for receiving and processing the inputs to operate the dialysis machine 100.

Dialysis system 101 depicted in FIGS. 1A and 1B may be the same or similar to the Liberty® Cycler produced by Fresenius Medical Care North America of Waltham, Massachusetts, United States of America. However, embodiments are not so limited, as FIGS. 1A and 1B depict an illustrative dialysis system according to one example. Embodiments may include, use, or be used in combination with various types of dialysis systems currently known to persons of skill in the art or developed in the future, including PD systems.

In some embodiments, a "dose" within a PD prescription may be described in terms of different variables. Illustrative and non-restrictive examples of variables may include fill volume ($V_{fill}$), the composition of the instilled PD fluid, especially the mass of the osmotic agent (e.g., glucose ($G_{dia}$), polyglucose, amino acids, and/or the like) and the duration of the dwell period ($T_{dwell}$). Given values of each of these dose variables may lead to specific intraperitoneal volume (IPV) trajectories (i.e., the variation of IPV with time).

Although glucose and $G_{dia}$ are used in examples in the present disclosure, embodiments are not so limited as this is for illustrative purposes only. More specifically, embodiments may operate with any type of osmotic agent capable of being used according to the present disclosure.

Figure 2:
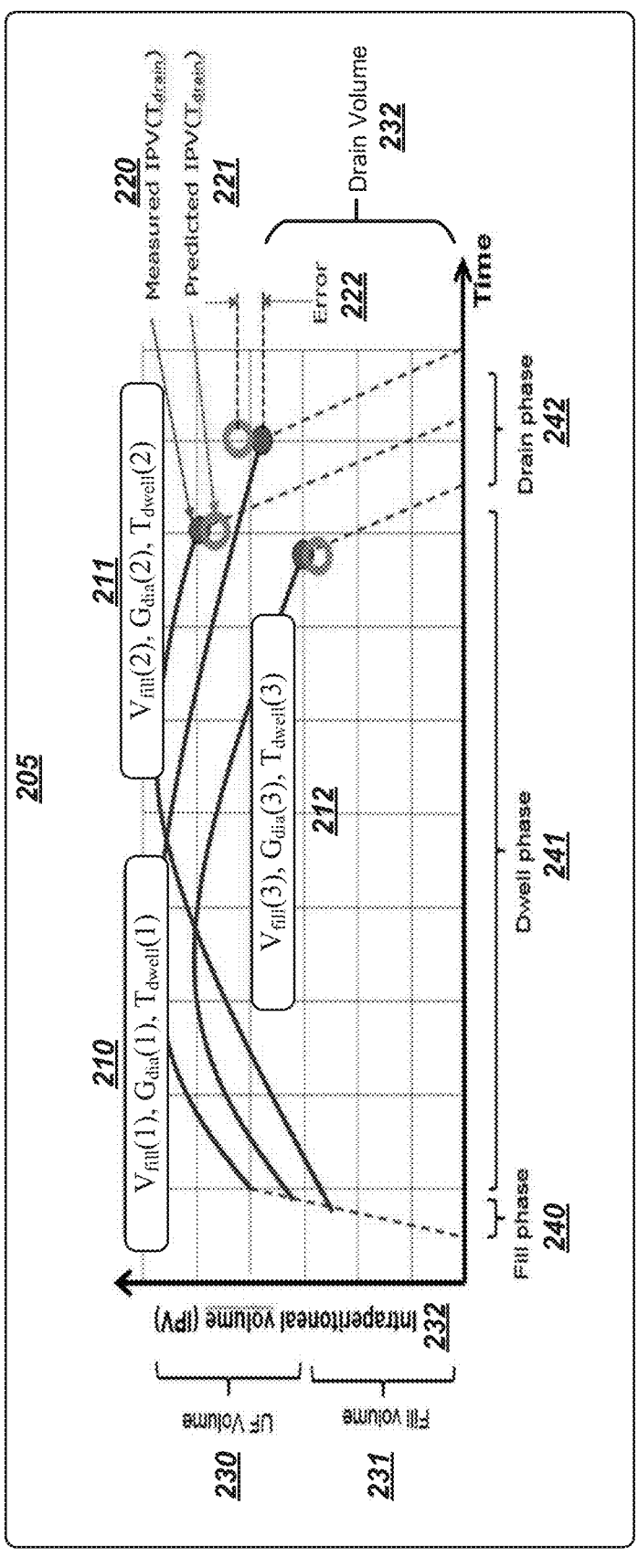
FIG. 2 depicts illustrative intraperitoneal volume (IPV) trajectories in accordance with the present disclosure.

FIG. 2 depicts illustrative IPV trajectories according to some embodiments. As shown in FIG. 2, graph 205 depicts IPV trajectories 210, 211, and 212 for given dosages (for instance, $V_{fill}$, $G_{dia}$, and $T_{dwell}$). IPV 232 may include a fill volume component 231 and a UFV component 230. Trajectories 210-212 are depicted over a PD treatment cycle having a fill phase 240, a dwell phase 241, and a drain phase 242. The resulting IPV at the time of the drain ($T_{drain}$) following the drain phase 242, the fill volume ($V_{fill}$) is subtracted from the drain volume 232 resulting in the UFV 230, the net volume of fluid removed from the patient during the cycle.

For each trajectory 210-212, a measured IPV ($T_{drain}$) 220 and a predicted IPV ($T_{drain}$) 221 may be determined. The difference between measured IPV ($T_{drain}$) 220 and predicted IPV ($T_{drain}$) 221 may be determined as an error value 222, indicating the difference between the predicted (or, in some instances, desired) value and the actual value for IPV ($T_{drain}$).

While the dose is considered one of the main predictors, other information may be introduced to further improve accuracy such as the time of day, hydration status, and/or the like. The error value may account for unknown or unpredictable effects leading to a difference between the measured and predicted (or, in some instances, desired or optimal) IPV. In some embodiments, the minimization of the error may be a basis for establishing the parameters of a computational model. Accordingly, in some embodiments, the measurements of IPV may be used to improve the prediction accuracy of a computational model configured according to some embodiments.

Figure 3:
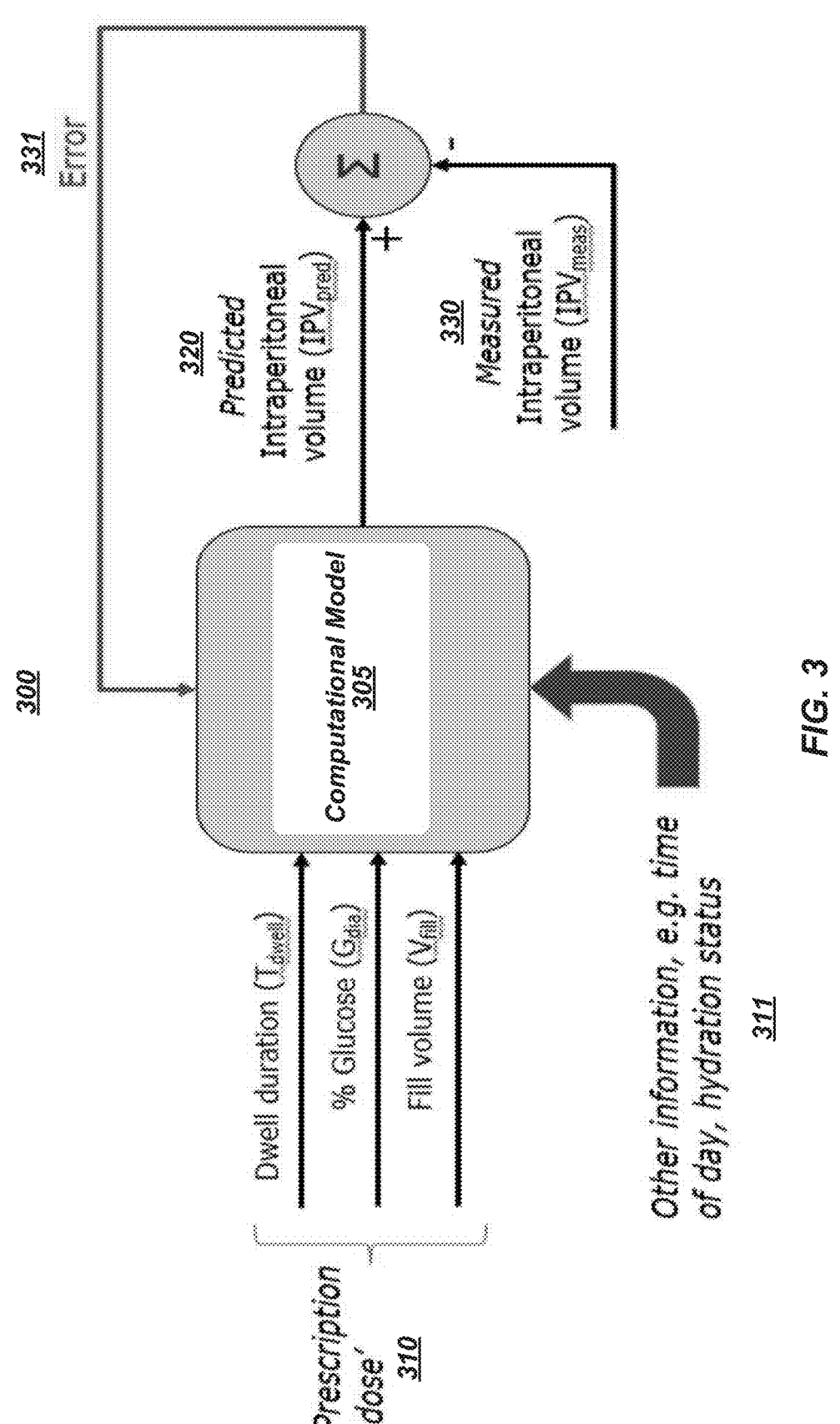
FIG. 3 illustrates a first exemplary operating environment in accordance with the present disclosure.

FIG. 3 illustrates a first exemplary operating environment in accordance with the present disclosure. As shown in FIG. 3, operating environment 300 may include a computational model 305 configured to receive input in the form of a prescription dose 310 and patient (or non-dosage) information 311. Non-limiting examples of patient information 311 may include time of day of treatment, hydration status, activity level, and/or the like. Computational model 305 may be trained to determine predicted IPV 320 using input 310, 311. An error value 331 may be determined based on a difference between predicted IPV 320 and a measured IPV 330. The error value 331 may be provided to computational model 305 to further train computational model 305, for example, to further improve the prediction accuracy of computational model 305.

Computational models used according to some embodiments, such as computational model 305, may be or may include an ML model, an AI model, a NN, an ANN, a CNN, a DL network, a DNN, a RNNs, combinations thereof, variations thereof, and/or the like. Embodiments are not limited in this context. In various embodiments, computational models may include linear models, regression models, phenomenological models, non-linear models, robust linear models, stepwise linear models, support vector machine (SVM) (e.g., Linear, Quadratic, Cubic, Fine, Medium, or Coarse Gaussian), Gaussian Process Regression (e.g., Squared, Exponential, Matern, Exponential, Rational Quadratic), regression learner, classification learner, combinations thereof, variations thereof, and/or the like. Embodiments are not limited in this context as computational models may be, may include, and/or may use any type of computational model now known or developed in the future.

In some embodiments, a computational model may be or may use a linear monotonic regression model. In various embodiments, a linear model may predict the IPV ($IPV_{Pred}$) from input variables considered to be independent. For example, the variables may include the glucose concentration ($G_{dia}$), the dwell duration ($T_{dwell}$), and the fill volume ($V_{fill}$) as the prescription "dose." The $IPV_{Pred}$ may be determined with a relationship of the form shown in the following Equations (1A) and/or (1B):

$$IPV_{Measured}(T_{drain}) = T_{dwell} + G_{dia} + V_{fill},$$

$$IPV_{Measured}(T_{drain}) = a + b \cdot T_{dwell} + c \cdot G_{dia} + d \cdot V_{fill}.$$

Besides the dose variables one or more of coefficients b, c, d, and an offset term a may be used (Equation (1B). In the language of experimental design, for example, there may be three factors (ascribing to main effects) and one response, representing a simple method to predict IPV. The parameters a, b, c and d may be unique to a specific patient and/or population of patients (for instance, a population of patients having at least one patient characteristic in common with the subject patient including, without limitation, age, gender, disease state, UFV range, physical characteristics (height, weight, and/or the like), error value or range, and/or the like). Multiple prescriptions lead to a matrix of doses variables and Equation (1) may be represented alternatively as the following Equation (2):

$$\begin{bmatrix} IPV_{measured}(1) \\ IPV_{measured}(2) \\ IPV_{measured}(3) \\ \cdots \\ IPV_{measured}(n) \end{bmatrix} = \begin{bmatrix} 1 & T_{dwell}(1) & G_{dia}(1) & V_{fill}(1) \\ 1 & T_{dwell}(2) & G_{dia}(2) & V_{fill}(2) \\ 1 & T_{dwell}(3) & G_{dia}(3) & V_{fill}(3) \\ \cdots & \cdots & \cdots & \cdots \\ 1 & T_{dwell}(n) & G_{dia}(n) & V_{fill}(n) \end{bmatrix} \cdot \begin{bmatrix} a \\ b \\ c \\ d \end{bmatrix}$$

After a certain number (for instance, four; the number of parameters in the regression model) PD cycles, the system of equations may become over determined and the parameters a, b, c, and d may be obtained by standard regression methods. The monotonic model may not capture the inherent non-linearity of the intraperitoneal volume (IPV) response. The typical IPV response is characterized by a rise after PD fluid instillation, reaching a peak IPV in the first few hours of the dwell before fluid reabsorption causes IPV to decrease (see, for example, FIG. 2).

Some embodiments may use a non-linear model with interactions. The linear model of Equations (1) and (2) may capture the first monotonic IPV increase. Accordingly, some embodiments may use a modified model structure according to the following Equation (3) (non-linear model by virtue of interactions between dose variables):

$$IPV = a + b \cdot T_{dwell} + c \cdot G_{dia} + d \cdot V_{fill} + b' \cdot T_{dwell} \cdot G_{dia} + c' \cdot T_{dwell} \cdot V_{fill} + d' \cdot G_{dia} \cdot V_{fill} + b'' \cdot G_{dia} \cdot T_{dwell} \cdot V_{fill}.$$

In the modified linear model, eight parameters [a, b, c, d, b', c', d', b''] are introduced with more degrees of freedom to also capture the nonlinearities of the interactions between the input variables and the IPV response. In some embodiments, the error term "a" in the model may account for disturbance effects from unknown factors as well as model limitations introduced by assuming relationships between dose variables. An example of unknown factors may include, without limitation, time of the dwell which influences the hydration status of the patient, patient activity during dwell, and/or the like. For example, if the patient was active during the dwell, the peak IPV may occur earlier than compared to a situation where the patient was inactive (for instance, chair-bound) during the cycle. Some embodiments may use activity factors, such as activity information input by the patient or caregiver and/or detected via an activity or patient monitoring devices (e.g., a device that monitors heart rate, steps, and/or the like, such as a Fitbit or Apple Watch device). In such embodiments, "activity" may be an additional factor which can be included in the model structure. Other factors or disturbances can be patient hydration status, food and fluid intake, time of the day, time elapsed into the dwell, and/or the like. In some embodiments, the factors or disturbances may be explicitly included in the model as parameters or lumped into the error term "a," if no information is available. In some embodiments, the parameters, disturbances, and/or factors may be determined based on historical information of a population of patients associated with the patient (for instance, sharing at least one characteristic of the patient, including, without limitation, age, gender, disease state, health condition (e.g., peritonitis and/ or staging thereof), UFV value or range, IPV value or range, dosage values, and/or the like)).

Figure 4:
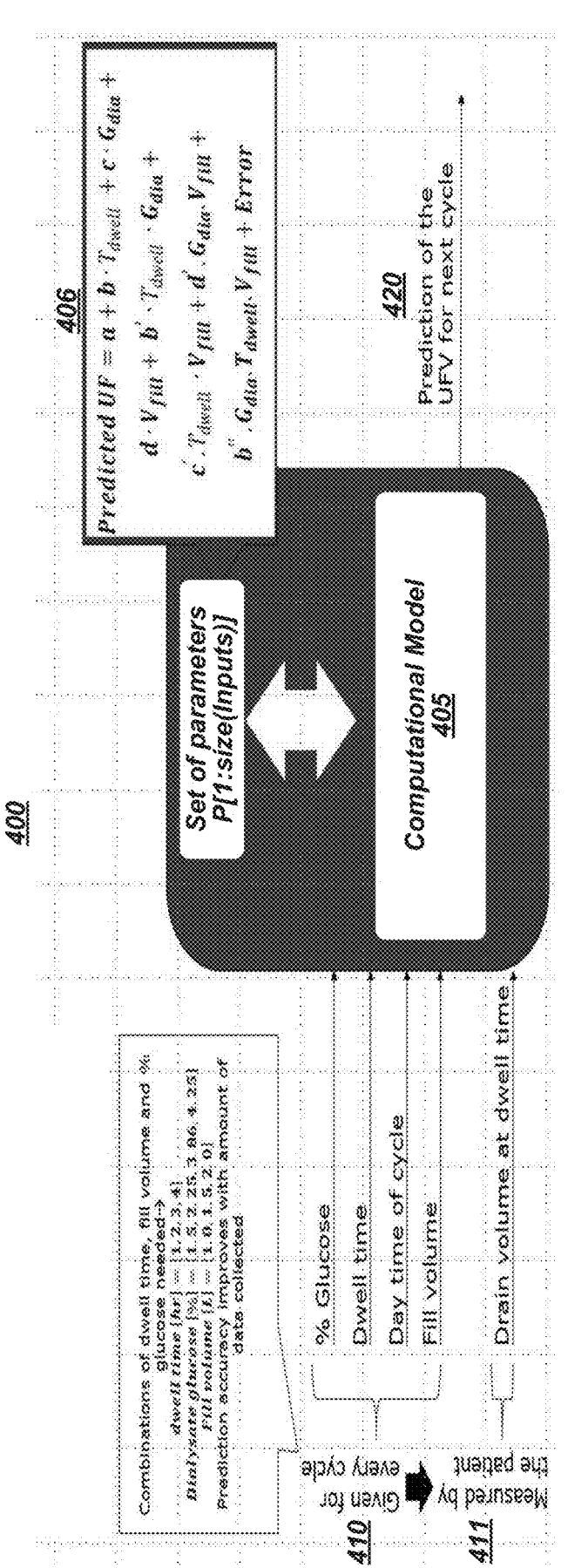
FIG. 4 illustrates a second exemplary operating environment in accordance with the present disclosure.

FIG. 4 illustrates an exemplary operating environment in accordance with the present disclosure. As shown in FIG. 4, operating environment 400 may include a computational model 405 configured to receive input 410, 411. Computational model 405 may use a model structure 406, such as Equation (3), to determine a UFV prediction 420.

In some embodiments, the linear models (i.e., Equations (1)-(3)) may be modified or extended to handle different variables. For example, a model structure may be modified to handle different osmotic agent properties. The following Equation (4) provides an extension of a linear model to handle colloid osmotic agent solutions (e.g., polyglucose) or mixtures of colloids and crystalloids:

$$\begin{aligned} IPV = &a + b \cdot T_{dwell} + c \cdot \text{Osmolarity}_{dia} + d \cdot V_{fill} + e \cdot \text{Colloid} \\ &\text{osmotic pressure}_{dia} + b' \cdot T_{dwell} \cdot \text{Osmolarity}_{dia} + \\ &c' \cdot T_{dwell} \cdot V_{fill} + d' \cdot \text{Osmolarity}_{dia} \cdot V_{fill} + \\ &b'' \cdot \text{Osmolarity}_{dia} \cdot T_{dwell} \cdot V_{fill} + e' \cdot T_{dwell} \cdot \text{Colloid} \\ &\text{osmotic pressure}_{dia} + f \cdot \text{Colloid osmotic} \\ &\text{pressure}_{dia} \cdot V_{fill} + g \cdot \text{Osmolarity}_{dia} \cdot \text{Colloid osmotic} \\ &\text{pressure}_{dia} + c'' \cdot \text{Colloid osmotic} \\ &\text{pressure}_{dia} \cdot T_{dwell} \cdot V_{fill} + c''' \cdot \text{Colloid osmotic} \\ &\text{pressure}_{dia} \cdot \text{Osmolarity}_{dia} \cdot V_{fill} + d'' \cdot \text{Colloid} \\ &\text{osmotic pressure}_{dia} \cdot \text{Osmolarity}_{dia} \cdot T_{dwell} + \\ &b''' \cdot \text{Colloid osmotic} \\ &\text{pressure}_{dia} \cdot \text{Osmolarity}_{dia} \cdot V_{fill} \cdot T_{dwell}. \end{aligned}$$

Some embodiments may use computational models with designed experiments (for instance, a "perturbation" approach). For example, a computational model may have the following three factors (control variables): (1) dwell time, (2) glucose concentration, (3) fill volume, and the rest of the factors may be captured in an error term or value. If the patient is perturbed with multiple combinations of dwell time, glucose concentration, and/or fill volume (i.e., computational model input), the computational model may output multiple values of IPV, which can provide an estimate of the model parameter set dependent on a chosen model structure. In some embodiments, data may be collected for discrete glucose concentrations and for discrete time.

The following is input information for a use case example:

Dwell time [hr]=[1,2,3,4];

Dialysate glucose [%]=[1.5,2.3,4.25];

Fill volume [L]=[1.0,1.5,2.0].

In the use case example, there are 3 factors and different levels for each factor, resulting in a total of 4×3×3=36 experiments based on full factorial design paradigm. The number of experiments may be reduced, for example, to 12 or another value by user selection or using fractional factorial experimental design by conducting only orthogonal experiments.

Once a model for an individual patient has been determined (model parameter set identified), the optimal dwell time may be generated for a given glucose concentration and fill volume. One assumption is that patient peritoneal membrane characteristics stay the same during multiple experiments. When membrane characteristics change, the predicted IPV will be systematically different from the measured IPV. Accordingly, the computational model may be used as an early detection tool to indicate some physiological changes, such as peritonitis. For instance, changes in the prescription, parameters, and/or UFV determined via the computational model may indicate a physiological change in the patient.

The model may be continuously trained or re-trained as more and more data are collected to provide, among other things, robust predictive capability of the model, e.g., tolerance to small variations in the measured UFV under identical dose variable conditions.

Figure 5:
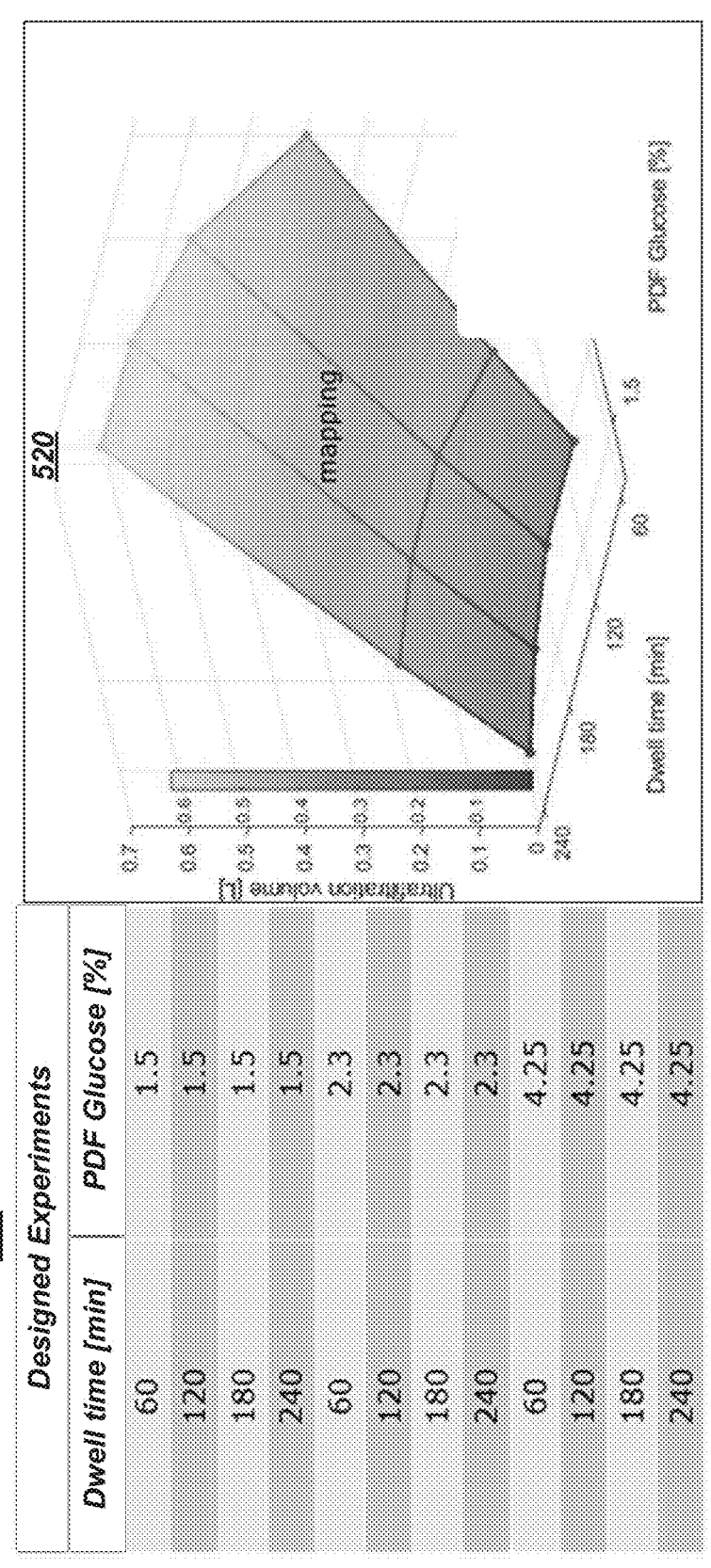
FIG. 5 depicts designed experiment model results in accordance with the present disclosure.

FIG. 5 depicts a simulation of how the statistical model may work in practice according to an example embodiment. For the purposes of simulation, a phenomenological model may be used to generate a temporal variation of IPV, for example, with the results of a model describing the IPV in terms of two dose variables 510 only so that a model may be visualized. Non-limiting examples of phenomenological models may include models described in Stelin et al., "A phenomenological interpretation of the variation in dialysate volume with dwell time in CAPD," Kidney International, Vol 38 (1990) pp. 465-472 ("Stelin et al."), which is incorporated by reference in the present disclosure as if fully set forth herein.

In the example depicted in FIG. 5, the variables 510 provide that the glucose in the PD dialysate is varied over the range 1.5%, to 4.25% and the dwell time varied over the range 60 min, to 240 min. The model results in a mapping 520 of the dose variables to the UFV. In some embodiments, generating the input data for the simulation may use a modified Rippe 3-pore-model, for example, to test an empirical model process. The model fitted to these data could then be used to predict future treatment cycles. In some embodiments, the accuracy may be improved, for example, by using more influencing factors for input into the model (e.g., time of day, activity, food and fluid intake, and/or the like).

Some embodiments may account for changes to the patient, such as changes in hydration status, peritonitis, and/or the like. To remove excess water from a PD patient, clinicians may prescribe: (1) dialysate osmotic agent concentration, (2) dwell time, typically set at 4 hours in CAPD patients, (3) fill volume, (4) number of cycles per day, and/or the like. Glucose is one of the osmotic agents which drives fluid transfer from capillaries to the peritoneal cavity. During PD treatment, the IPV increases and reaches a peak. In most cases, the patient's treatment schedule is set to a specific fill volume, dwell time and % glucose of the dialysate with multiple cycles per day. If all cycles are performed with the same initial conditions, with respect to the time of the specific cycle of the day, the drain volume should only vary because of overhydration, dehydration, and membrane changes (e.g., peritonitis, fibrosis, neovascularization).

In some embodiments, the patient and/or caregiver can put in at the start of PD various patient information, such as a schedule for every cycle, and then update the data at every following cycle, using, for instance, a software application (or mobile device "app" or "dialysis analysis application"). Illustrative and non-limiting inputs may include % glucose of the dialysate (one of the possible solutions: 1.36%, 1.5%, 2.3%, 3.86%, 4.25% etc.), fill volume (for example, 2 L), dwell time (for example, 4 hr), number of cycles per day (for example, 4), time of day of the weighing of the drain bag, and/or the like. Illustrative and non-limiting measured values may include: drained volume (L) or weight (Kg), UFV (drain volume (L)–fill volume (L)), cycle start time (drain time–dwell time), and variations in dwell time.

Some embodiments may operate to detect changes in the peritoneal membrane caused, for example, by peritonitis. The principle relies on the UFV being predictable, especially where there is consistency in the prescription in terms of dose variables. A measured set of UFV values that are systematically different from the predicted UFV indicates a change in peritoneal membrane transport. In the case of a peritonitis episode, the contribution of the large pores of the membrane may become more significant, While the larges pore permit protein transport, it can have the negative effect of increased glucose absorption, reducing the resulting UFV. The following Equation (7) provides a possible regression model that may be employed in such a diagnostic application:

$$UFV = a + b \cdot T_{dwell} + c \cdot T_{STC}$$

Where UFV is the measured variable or output variable; the dwell time and the start time of the cycle could vary. The glucose concentration and fill volume are constant for every cycle, The following Equation (8) is a more sophisticated model structure, although many other structures are also possible as highlighted earlier:

$$UFV = a + b \cdot T_{dwell} + c \cdot T_{STC} + d \cdot T_{dwell} \cdot T_{STC}$$

In both Equations (7) and (8), the error term "a" in the model may account for disturbance effects from unknown factors. An example of an unknown factor may include the patient's activity during the dwell time.

In general, the variables a, b, c, and d (and alternatives, such as a', b', etc.) may be coefficients, such as regression model coefficients. The form of the coefficients may depend on the form of the model selected, the various predictor variables involved, properties of the patient's membrane transport characteristics, and/or the like. The coefficients may be unique to every patient for a limited period of time. Changes in a, b, c, d in the same patient is possible over time (weeks to months), e.g., due to anatomical changes to the membrane, activity levels, fluid intake, and/or the like.

If the treatment prescription is unchanged over many cycles and small variations in the timing of the drain and the dwell duration are captured, multiple values of UFV may be obtained, providing a robust determination of the regression model coefficients (for a chosen model structure).

If for example, the number of cycles per day is 4 with a variation of approximately 30 minutes in the start time of the cycle, and the dwell duration is 4 hours with approximately 10% variation, the following input variables could be generated each day:

Dwell time [hr]=[4±10%,4±10%,4±10%,4±10%];

Start time of the cycle [hr]=[8:00±0:30;12:00±0:30; 16:00±0:30;20:00±0:30].

In this example, there are only two factors and different levels for each factor, resulting in a total of 4×4=16 experiments, for example, based on a full factorial design paradigm. With these inputs and a suitable regression model, the UFV may be predicted for the next cycle dependent on the time of day (which may have some relation to the hydration status of the patient). After performing the cycle, the UFV is measured by the patient and the error between predicted and measured UFV is obtained.

Using the following Equation (9), the relative error between the predicted UFV for the specific cycle and the measured UFV by the weighing of the drain volume may be determined:

$$\% \ ERROR = \frac{UFV_{measured} - UFV_{predicted}}{UFV_{measured}}$$

According to some embodiments, the error signal may be used to guide the optimization process from which the optimal values of the regression model coefficients are identified.

Figure 6:
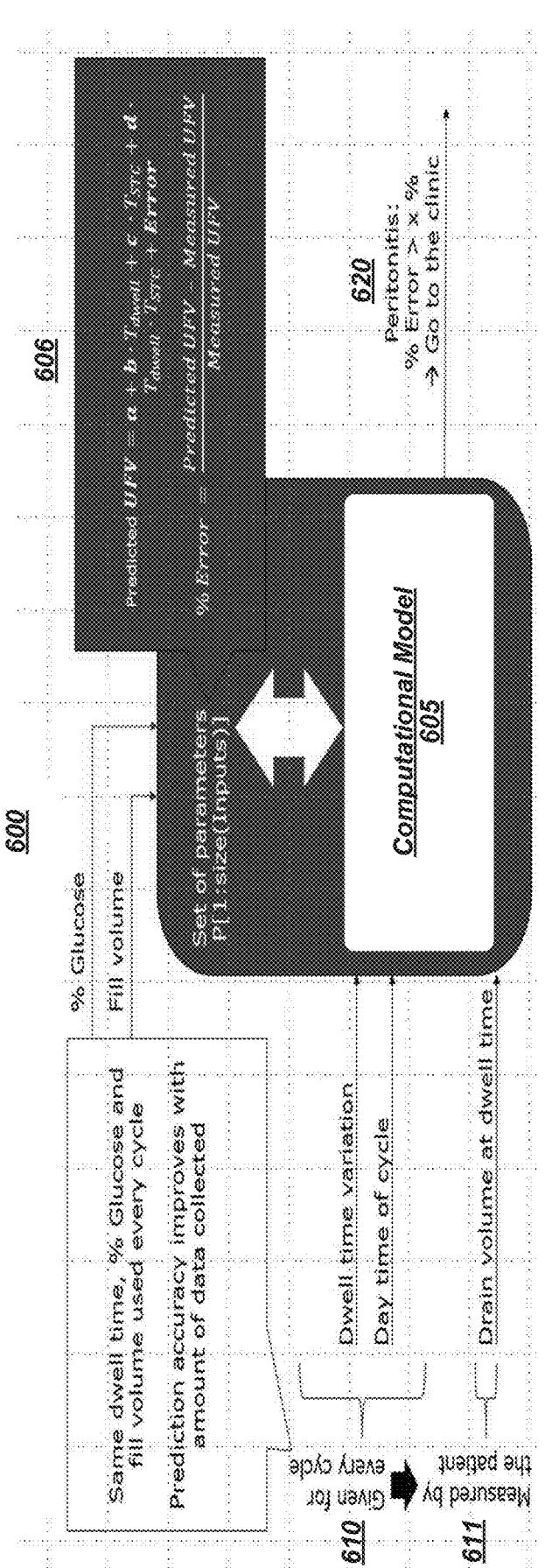
FIG. 6 illustrates a third exemplary operating environment in accordance with the present disclosure.

FIG. 6 illustrates an exemplary operating environment in accordance with the present disclosure. As shown in FIG. 6, operating environment 600 may include a computational model 605 configured to receive input 610, 611. Computational model 605 may use a model structure 606, such as Equations (8) and (9), to determine a peritonitis prediction 620. For instance, if the error value or percentage is over a threshold, a peritonitis condition may be predicted.

Figure 7:
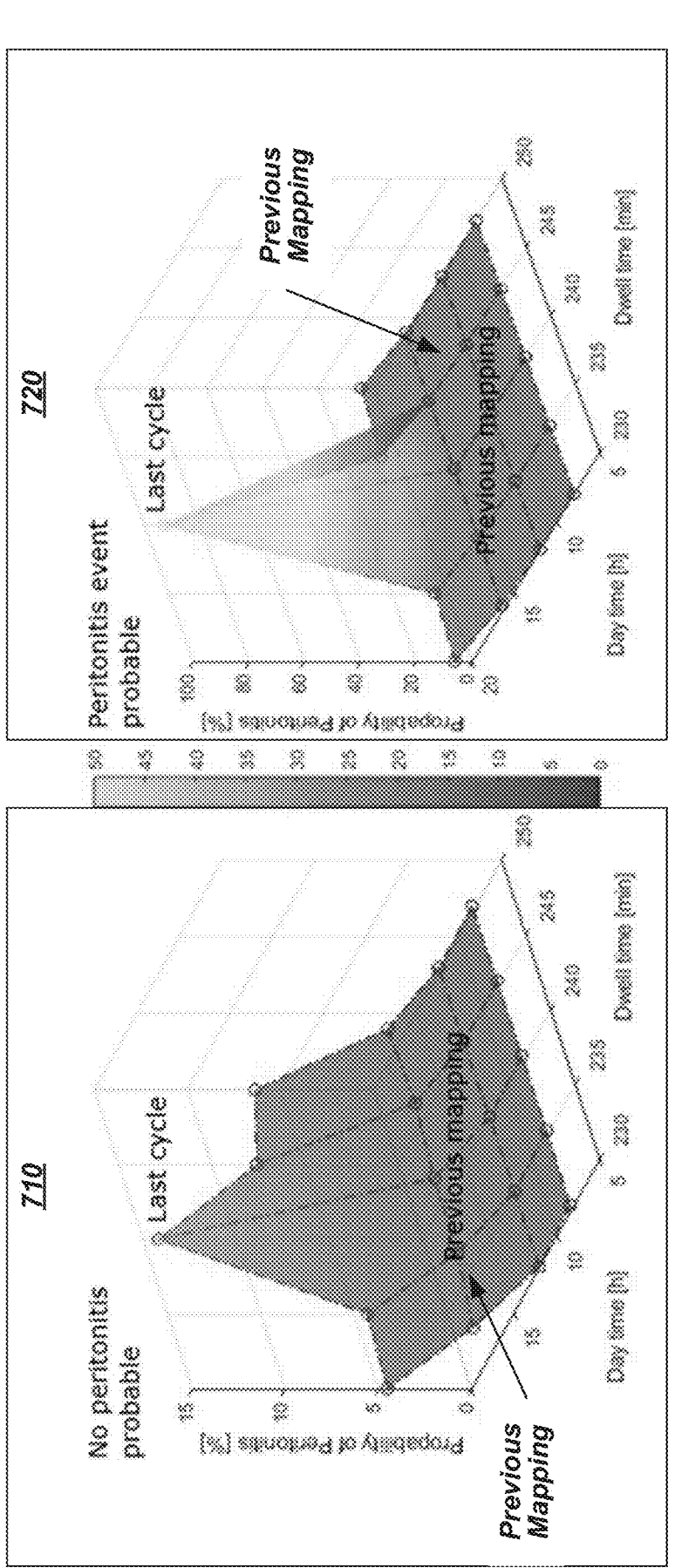
FIG. 7 depicts peritonitis prediction information in accordance with the present disclosure.

FIG. 7 depicts peritonitis prediction information according to some embodiments. Graph 710 shows the case of low probability of peritonitis. Graph 720 shows a high probability of peritonitis for the last cycle performed. For example, the last cycle performed uses a dwell time of 240 min and a start day time of 20:00 h. For all the input data with additional measurement of the UFV at dwell time, the difference in percent between predicted and measured UFV is calculated. As the deviation in UFV increases, the probability of peritonitis or other membrane issues drastically increases. Accordingly, in some embodiments, an early warning system for peritonitis may be implemented.

Figure 8:
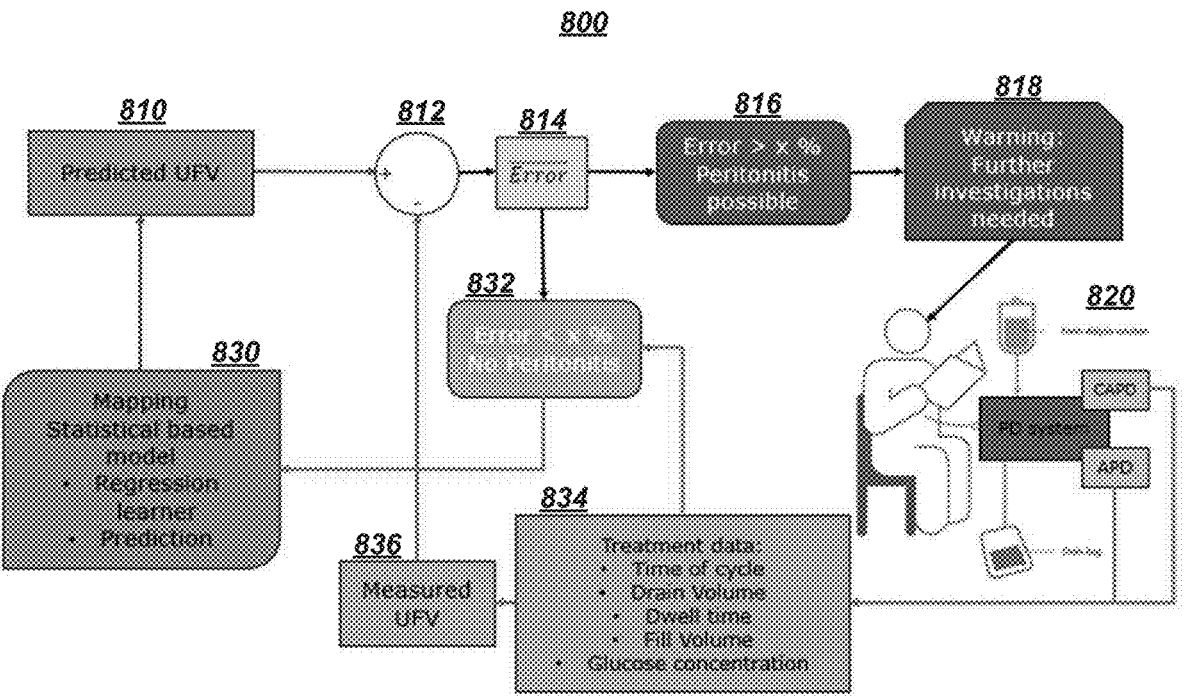
FIG. 8 illustrates a fourth exemplary operating environment in accordance with the present disclosure.

FIG. 8 illustrates an exemplary operating environment in accordance with the present disclosure. As shown in FIG. 8, operating environment 800 may implement a computational model approach with ML, AI, NN, CNN, regression models, phenomenological models, and/or the like for continuous optimization of the model parameters. In one example, the data generated every cycle may be used to train or re-train a computational model. In another example, with a regression learner, the data generated during every cycle could be feedback as an additional dataset to a matrix which could be used to optimize the model parameters. With this procedure the prediction accuracy could be further improved with the time of treatment.

The model system of operating environment 800 may include a predicted (or desired, optimized, or targeted in some examples) UFV value 810 determined according to UFV determination processes 830 based on treatment data 834. A measured UFV 836 may be determined based on a patient PD treatment via a PD system 820. Measured UFV 836 may be compared 812 to (for instance, subtracted from) predicted UFV 810 to determine an error value 814 (for instance, an absolute value). If the error value 814 is over a threshold value 816, then the patient or caregiver may be warned that peritonitis (or other health condition) is possible and further investigations may be needed 818. If the error value is below a threshold value 832, then the information may be provided to the computational model 830, for example, for training or re-training. The model 830 may be continuously updated, such as after every cycle, using data collected from all historical treatments (dwell time, start time of cycle, drain volume data, and/or the like).

A UFV determination process according to some embodiments may include a learning process and/or a prediction process.

In the learning process mode, multiple prescriptions (with predefined dose variables) may be used to program a PD treatment system and the resulting UFV may be measured following each cycle of treatment. The dose variables may be fed into a UVF optimizer computational model along with patient information, such as the time of day, hydration status, activity level, and/or the like. The learning process may be used for designed experiments. The UFV optimizer model may operate to generate a predicted UFV, which may be compared with the measured UFV to determine an error. In some embodiments, the error may be minimized by adaptation of the model parameter set (i.e., the coefficients of the model regression equations).

Figure 9:
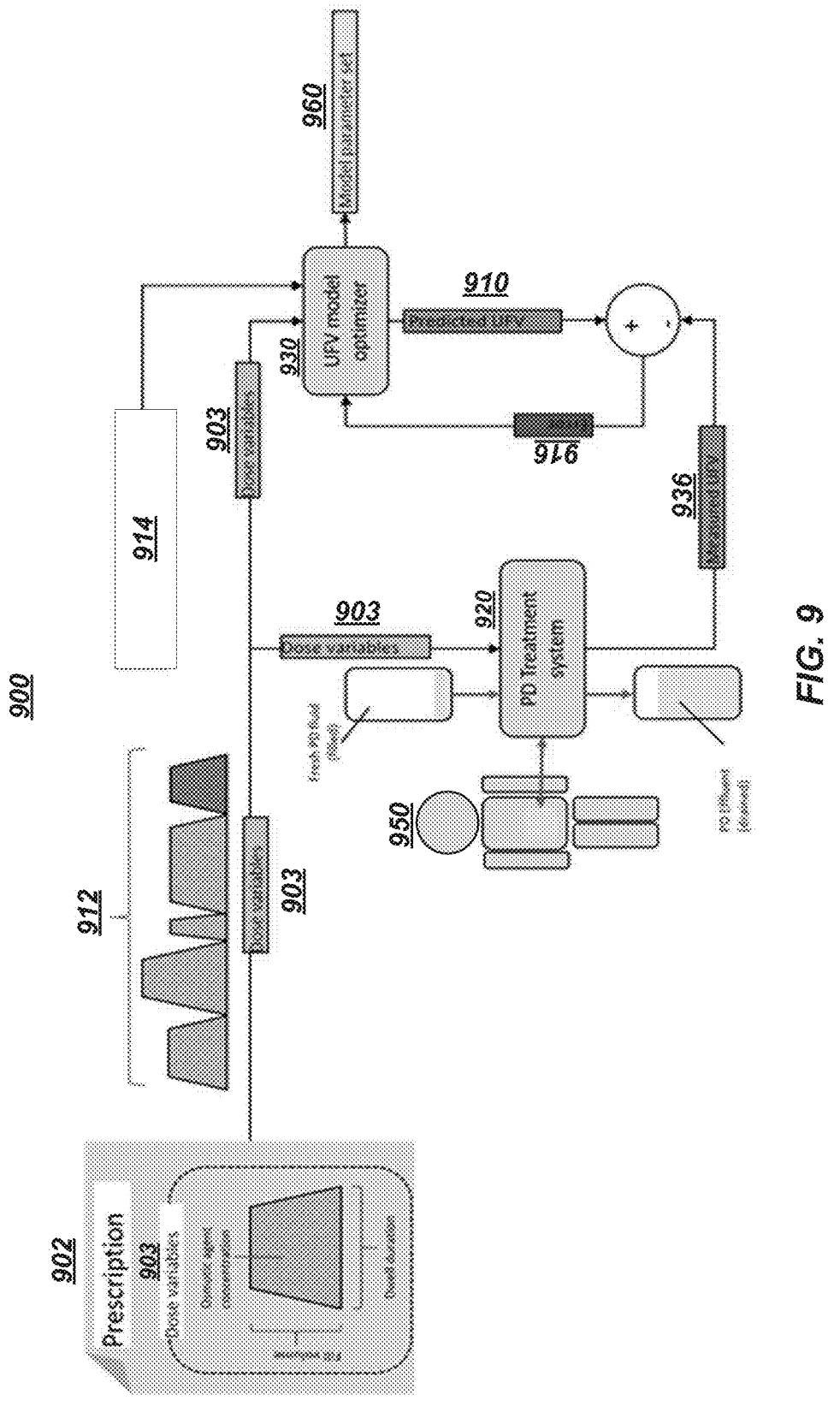
FIG. 9 illustrates a fifth exemplary operating environment in accordance with the present disclosure.
Figure 29:
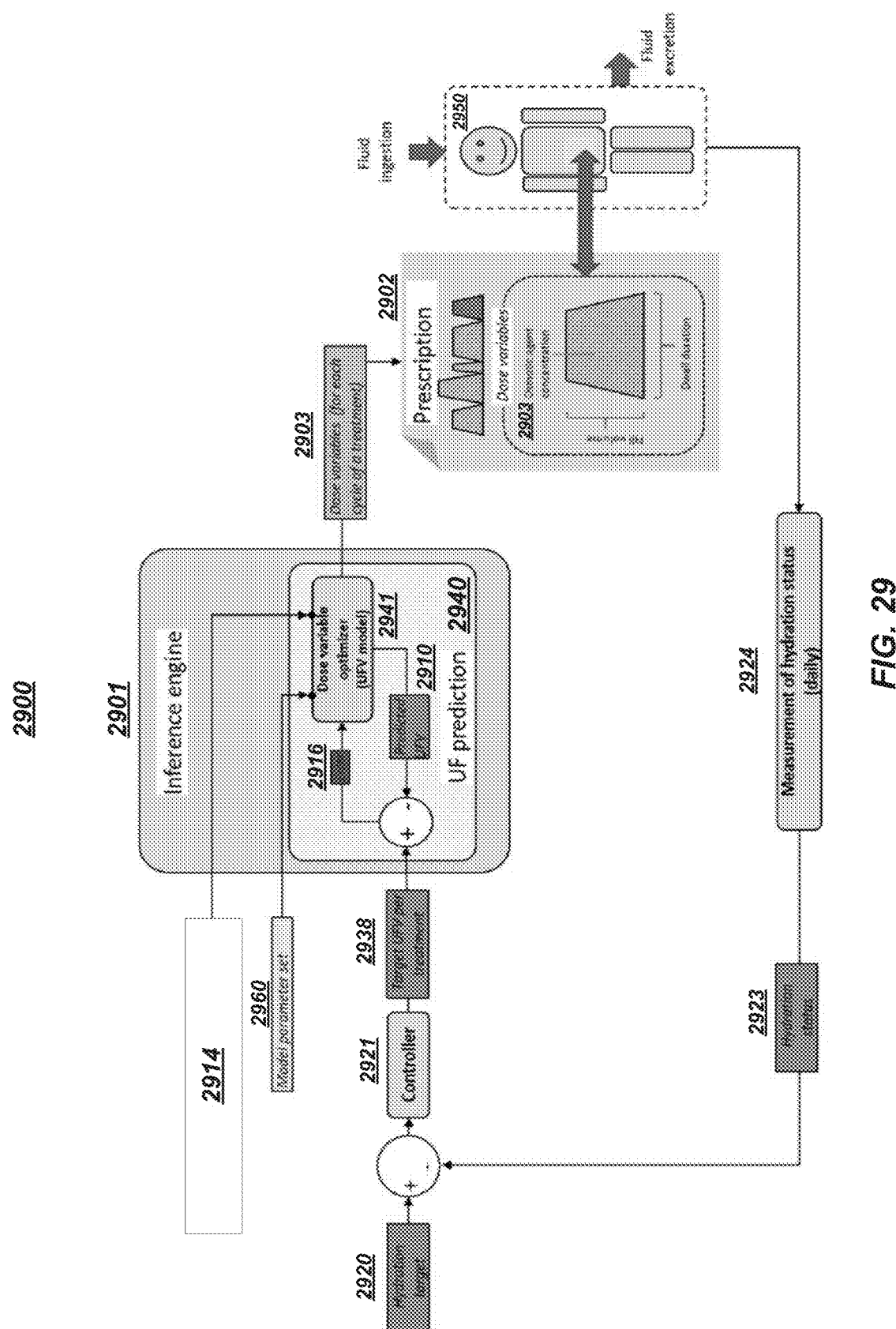
FIG. 29 illustrates an eighth exemplary operating environment in accordance with the present disclosure.
Figure 30:
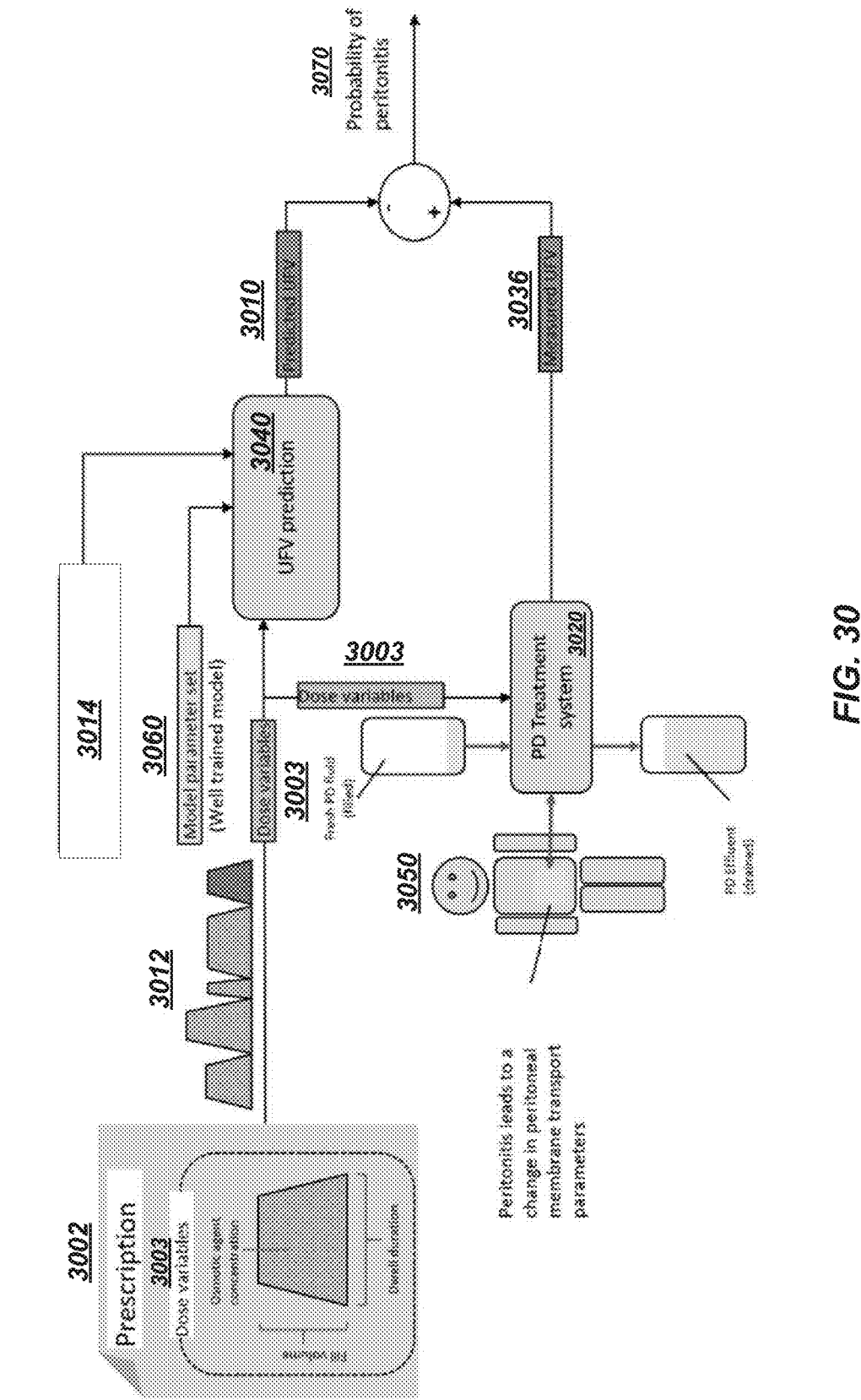
FIG. 30 illustrates a ninth exemplary operating environment in accordance with the present disclosure.

FIG. 9 illustrates an exemplary operating environment in accordance with the present disclosure (see also, FIGS. 29 and 30). More specifically, FIG. 9 depicts a learning process 900 that includes determining a prescription 902 with dose variables 903. In some embodiments, the dose variables 903 may include a fill volume, fill duration, and/or an osmotic agent concentration. The dose variables 903 may be included in a design experiment 912. In various embodiments, design experiment 912 may include a sequence of PD cycles that involve different combinations of dose variables 903 performed on a patient 950 via a PD treatment system 920. A measured UFV 936 may be determined for some or all cycles.

In some embodiments, dose variables 903 (and unknown factors 914, such as patient information, time of day, activity levels, etc.) may be provided to a UFV optimizer model 930 configured to generate a predicted UFV 910. In various embodiments, predicted UFV 910 may be compared with measured UFV 936 to determine an error 916. UFV optimizer model 930 may operate to determine a model parameter set 960 (i.e., the coefficients (for instance, a, b, c, and/or d) of the model regression equations) to minimize error 916.

Figure 10:
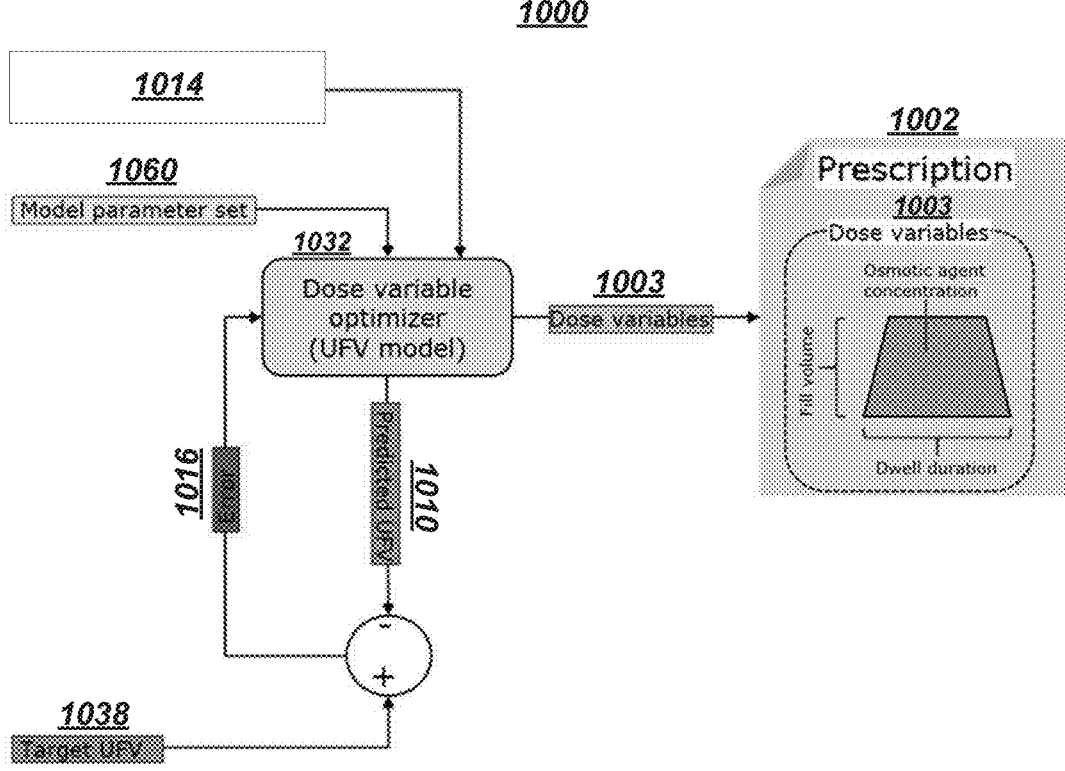
FIG. 10 illustrates a sixth exemplary operating environment in accordance with the present disclosure.

During the prediction process, the model parameter set may be used to predict the UFV. FIG. 10 illustrates an exemplary operating environment in accordance with the present disclosure (see also, FIGS. 29 and 30). More specifically, FIG. 10 depicts an operating environment 1000 for a prediction process according to some embodiments. As shown in FIG. 10, a dose variable optimizer model 1032 may receive patient information 1014 and a model parameter set 1060 as input. Dose variable optimizer model 1032 may operate to adapt dose variables 1003 of a prescription 1002 to minimize an error 1016 between a predicted UFV 1010 and a target UFV 1038. Accordingly, the value of each dose variable 1003 may be used in a PD treatment process to minimize error 1016.

In some embodiments, the UFV optimizer model may operate to map the given dose variables to the corresponding measurements of UFV. In various embodiments, statistical regression models may be used that can provide an acceptable mapping (the predicted UFV is close to the measured UFV), but do not necessarily bear any relationship to the underlying physical principles.

The way in which regression models may be used for UFV prediction may be illustrated by simulation of measured UFV values. A non-limiting example of generating simulated data may be the same or similar to techniques described in Stelin et al. For example, these simulated UFV values may be generated via a phenomenological model. In various embodiments, simulated UFV values may be determined via a phenomenological model, the following Equation (10), and applying different dose variable conditions:

$$IPV(t)=V_{Fill}+UFV(t)=V_{Fill}+a_1(1-e^{-kt})-a_2t,$$

where IPV is the intraperitoneal volume (the cavity volume), UFV is the ultrafiltration volume, $V_{fill}$ is the initial volume instilled into the peritoneal cavity, k is a decay constant representing transport process such as glucose absorption, $a_1$ describes the maximum 'static' UF volume achieved which is a consequence of the applied concentration of the osmotic agent (usually glucose), $a_2$ characterizes a fixed rate of absorption of the dialysate in the peritoneal cavity The following Table 1 provides illustrative coefficient values:

TABLE 1

| a₁ | V_Fill | k | a₂ |
|---|---|---|---|
| 1015 (Glucose = 3.68%) | 2050 | 0.0115 | 1.25 |
| 585 (Glucose = 2.3%) | 2050 | 0.0115 | 1.25 |
| 325 (Glucose = 1.36%) | 2050 | 0.0115 | 1.25 |

In some embodiments, Table 1 provides example values of the coefficients in Equation (10) used to generate a range of IPV (or UFV) values due variation in osmotic agent concentration (% glucose), while fill volume and dwell duration are maintained constant.

Figure 11:
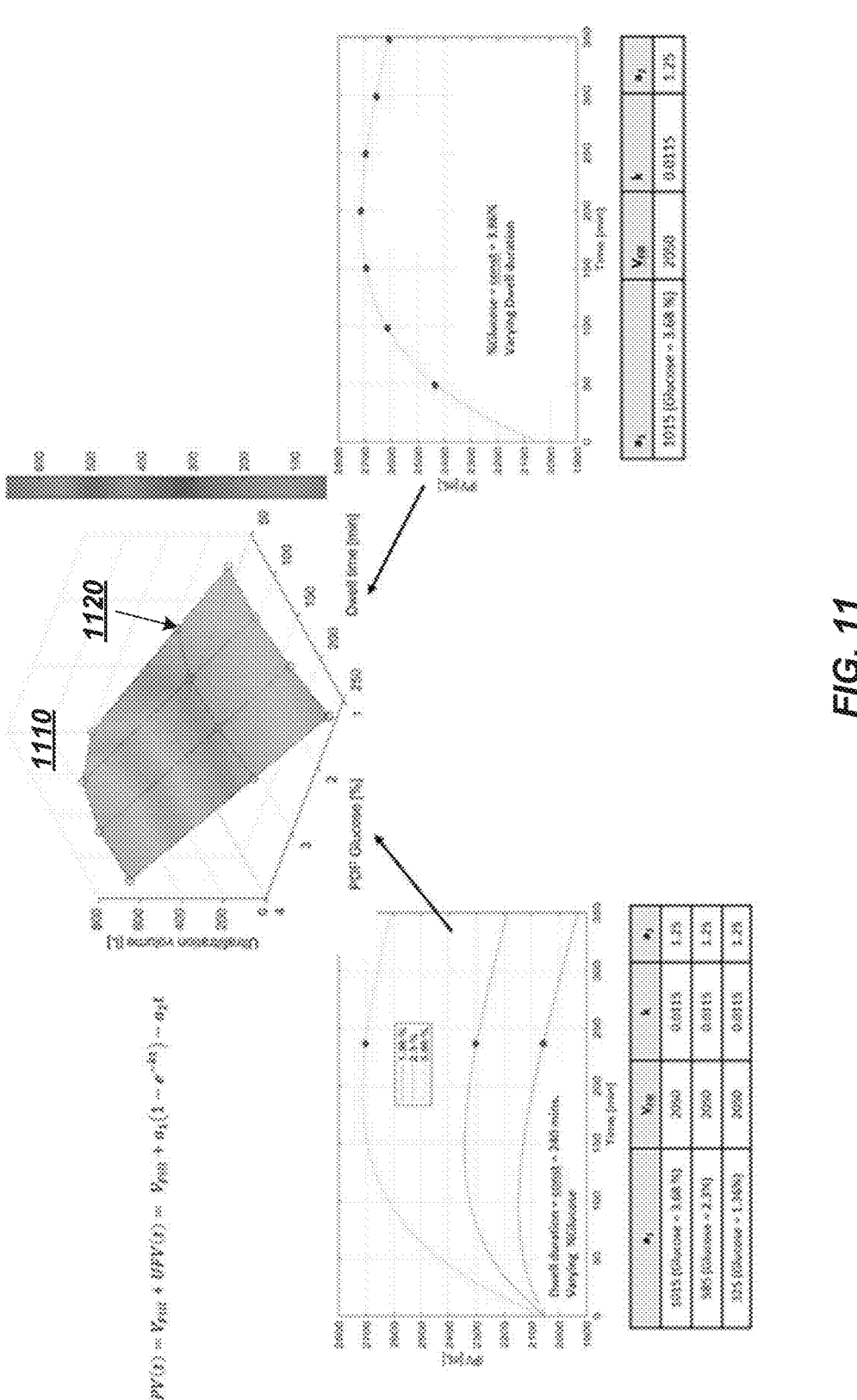
FIGS. 11-13 depict designed experiment model results in accordance with the present disclosure.

Repeating the process for increments in dwell duration, may lead to a vector of UFV values determined by variation in osmotic agent concentration and dwell duration. With only two dose variables, the UFV range may be visualized as a surface 1120 as shown in graph 1110 of FIG. 11.

A suitable regression equation may be introduced to recreate the UFV surface, that is an equation that maps the dose variables to the UFV. For example, the following Equation (11) provides a simple monotonic linear form (Regression Model 1):

$$UFV_{Pred}(t) = a + b \cdot [Glu] + c \cdot T_{dwell},$$

where Glu is the concentration of the osmotic agent such as glucose and $T_{dwell}$ is the dwell duration.

The optimization method determines the values of the coefficients a, b, c in order to reproduce, as closely as possible, the measured UFV values. A non-limiting example, of an optimization method may include a "least squares" process. The coefficients of Regression Model 1 are shown in Error! Reference source not found. and these are unique to the fictitious patient described by the phenomenological model previously described in the present disclosure. The predicted UFV for a different patient, with different membrane transport characteristics for example would be described with a different set of coefficients in the regression model:

TABLE 2

| Coefficient | Value |
|---|---|
| a | −269.32 |
| c | 0.2903 |
| b | 210.93 |

Figure 12:
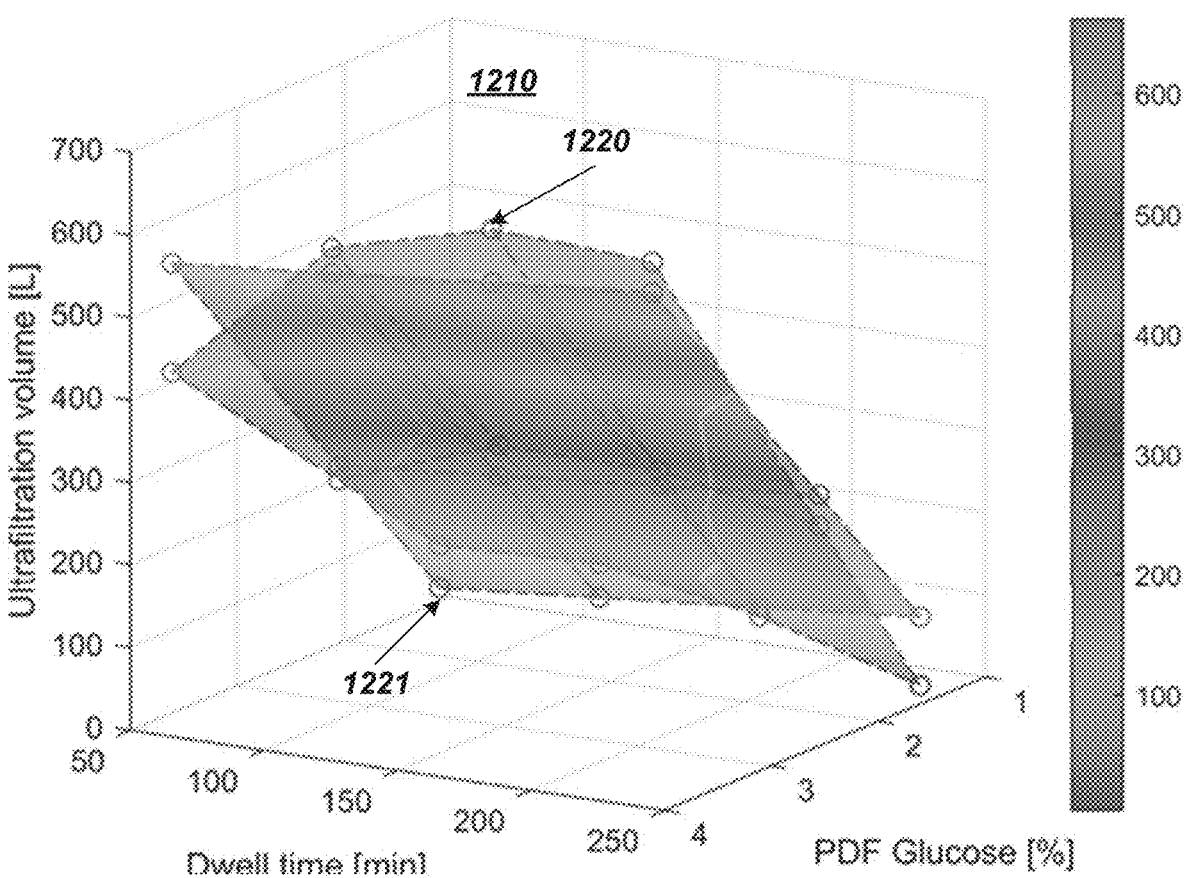

The performance of Regression Model 1 may be visualized by comparison of the resulting surface plot for UFV against the 'measured UFV' values generated from the phenomenological model. FIG. 12 depicts a graph 1210 comparing the measured UFV plot 1220 with a simulated plot 1221.

In some embodiments, an enhancement of Regression Model 1 might be to generate an array of Regression Model 1 results, graphs, etc., that may be used for specific restricted ranges of the osmotic agent concentration or the dwell duration. This approach may generate a matrix of regression model coefficients. The form of the regression model may be further illustrated with a more sophisticated rendition such as "Regression Model 2," provided in the following Equation (12):

$$UFV_{Pred}(t) = a + b \cdot [Glu] + c \cdot T_{dwell} + d \cdot [Glu]^2 + e \cdot [Glu] \cdot T_{dwell} + f \cdot T_{dwell}^2.$$

In one example of Regression Model 2, the resulting coefficients that provide optimal mapping between the dose variables and the measured UFV are given in the following Error! Reference source not found.

TABLE 3

| Coefficient | Value |
|---|---|
| a | −172.1 |
| b | 113.1 |
| c | 1.131 |
| d | −0.2919 |
| e | 0.6624 |
| f | −0.00834 |

Figure 13:
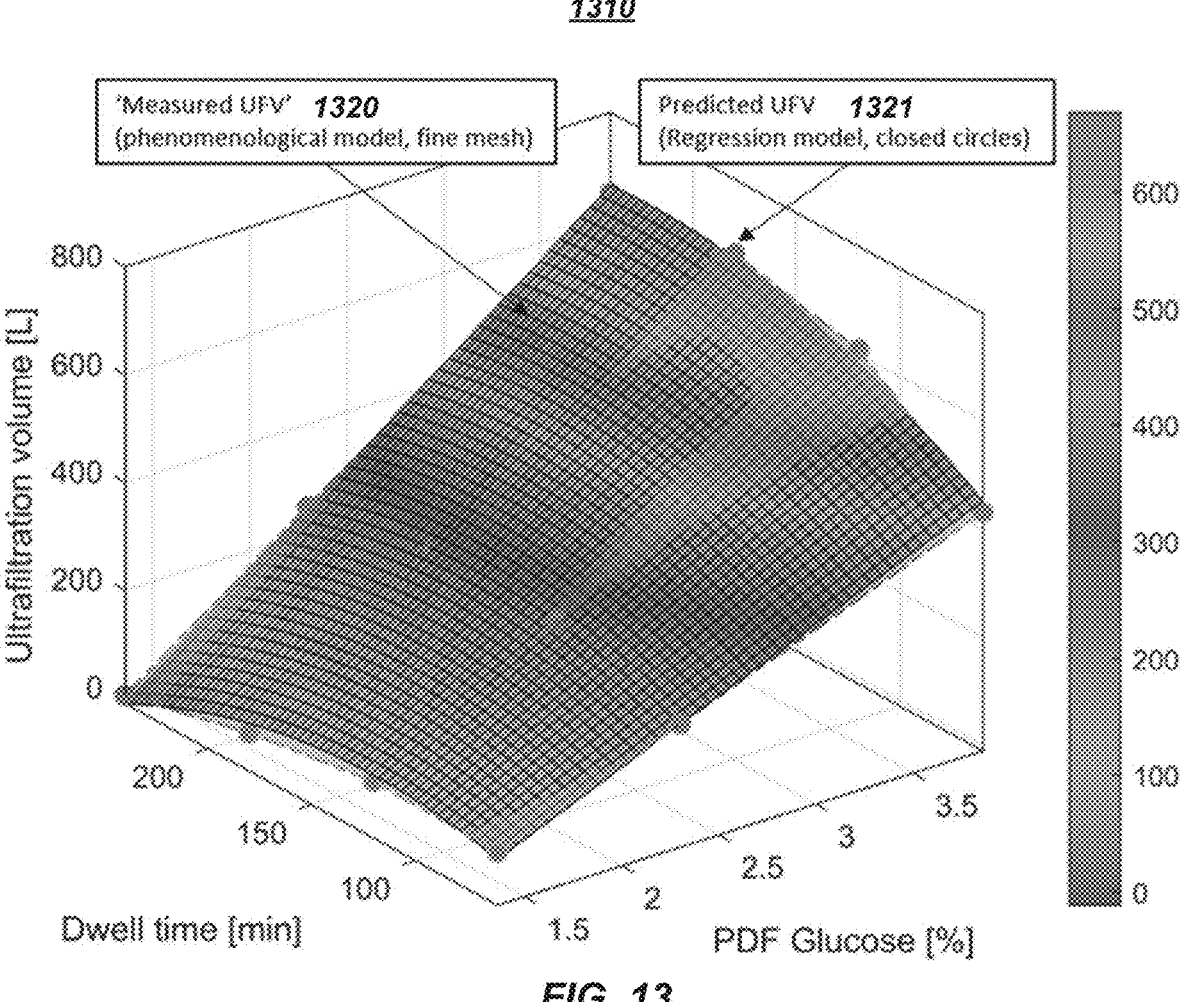

The performance of Regression Model 2 may be visualized as shown in FIG. 13 by graph 1310 depicting a comparison of the resulting surface plot for UFV 1321 against the 'measured UFV' values generated from the phenomenological model 1320.

Regression Model 2 resembles much more closely the 'measured UFV' data, illustrating the importance of considering the form of the regression model. On the one hand, the choices of regression model are limitless in terms of the number of predictor variables and regression model form. On the other hand, more complex model forms run the risk of instability especially where predictor terms of degree 2 of high are involved. Often the compromises in any practical setting, relate to the number of predictor variables available and the number of designed experiments and therefore time needed to train the model. Where the number of predictor variables becomes large, principal component analysis is useful in identifying only those predictors of significant influence. Accordingly, predictors of significant influence may be determined according to some embodiments described in the present disclosure.

Figure 14:
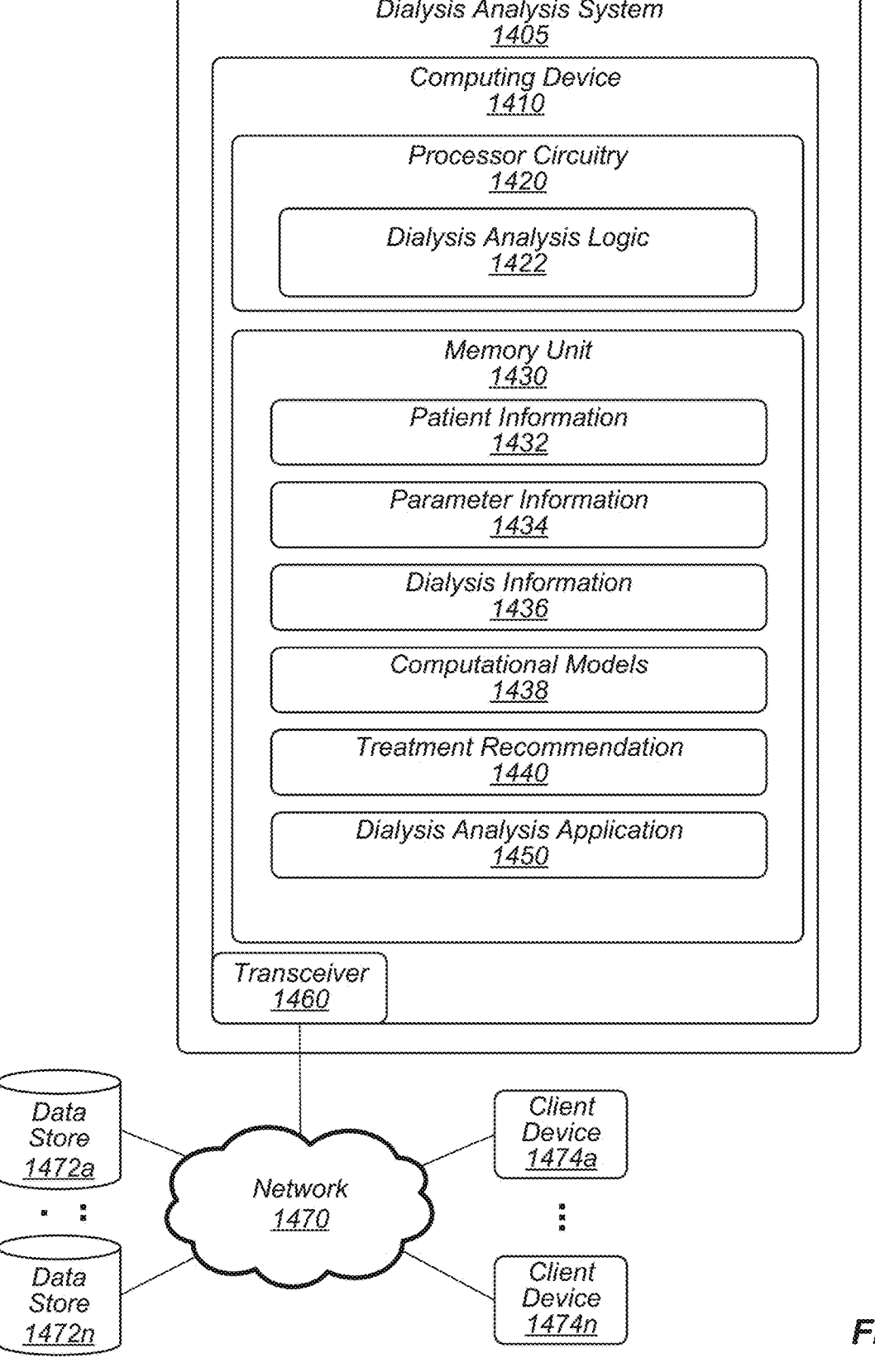
FIG. 14 illustrates a seventh exemplary operating environment in accordance with the present disclosure

FIG. 14 illustrates an example of an operating environment 1400 that may be representative of some embodiments. As shown in FIG. 14, operating environment 1400 may include a dialysis analysis system 1405. In various embodiments, dialysis analysis system 1405 may include a computing device 1410 communicatively coupled to network 1470 via a transceiver 1460. In some embodiments, computing device 1410 may be a server computer or other type of computing device.

Computing device 1410 may be configured to manage, among other things, operational aspects of a dialysis analysis process, PD optimization process, and/or UFV determination process according to some embodiments. Although only one computing device 1410 is depicted in FIG. 14, embodiments are not so limited. In various embodiments, the functions, operations, configurations, data storage functions, applications, logic, and/or the like described with respect to computing device 1410 may be performed by and/or stored in one or more other computing devices (not shown), for example, coupled to computing device 1410 via network 1470 (for instance, one or more of client devices 1474a-n). A single computing device 1410 is depicted for illustrative purposes only to simplify the figure. Embodiments are not limited in this context.

Computing device 1410 may include a processor circuitry that may include and/or may access various logics for performing processes according to some embodiments. For instance, processor circuitry 1420 may include and/or may access a dialysis analysis logic 1422. Processing circuitry 1420, dialysis analysis logic 1422, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 2600. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, variations thereof, combinations of any of the foregoing, and/or the like.

Although dialysis analysis logic 1422 is depicted in FIG. 14 as being within processor circuitry 1420, embodiments are not so limited. For example, dialysis analysis logic 1422 and/or any component thereof may be located within an accelerator, a processor core, an interface, an individual processor die, implemented entirely as a software application (for instance, a dialysis analysis application 1450) and/or the like.

Memory unit 1430 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 1430 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 1430 may store various types of information and/or applications for an dialysis analysis process according to some embodiments. For example, memory unit 1430 may store patient information 1432, parameter information 1434, dialysis information 1436, computational models 1438, treatment recommendations 1440, and/or an dialysis analysis application 1450. In some embodiments, some or all of patient information 1432, parameter information 1434, dialysis information 1436, computational models 1438, treatment recommendations 1440, and/or an dialysis analysis application 1450 may be stored in one or more data stores 1472a-n accessible to computing device 1410 via network 1470. For example, one or more of data stores 1472a-n may be or may include a HIS, an EMR system, a dialysis information system (DIS), a picture archiving and communication system (PACS), a Centers for Medicare and Medicaid Services (CMS) database, U.S. Renal Data System (USRDS), a proprietary database, and/or the like.

In some embodiments, dialysis analysis logic 1422, for example, via dialysis analysis application 1450, may operate to perform a PD optimization process and/or UFV determination process according to some embodiments. In various embodiments, dialysis analysis application 1450 may operate as a peritonitis prediction application (or "app") and/or PD optimization application for a patient or caregiver using processes according to some embodiments.

In some embodiments, a feedback control process with continuous Intraperitoneal Pressure (IPP) and hydration status measurements can be used to keep the hydration status of the patient within a target level range. The feedback control process may use a feedback controller (for example, a PID) or a more complex so-called expert system with the target hydration status, the current hydration status of the patient measured by BCM (body composition monitor), weighing in combination with known dry weight concepts and continuous IPP measurements, UFV measurements at the end of the dwell, a UFV prediction model (e.g., statistical or first principles). In some embodiments, the controller may operate to automatically optimize the UFV for each cycle by adjusting the dwell time, fill volume, and/or, if necessary, osmotic agent (OA) concentration to keep the patient on target hydration status (HS). The controller may be combined with processes described according to the present disclosure.

The feedback control process may operate using PD systems with different configurations. For example, two different possibilities to supply the patient with dialysate are possible, using dialysate bags or using a dialysate on the fly mixing system. With dialysate bags, only discrete OA concentrations available on the market could be used. The on the fly mixing of dialysate dependent on the patients' needs would deliver a further adjustment to individualize the treatment, for example, to avoid unnecessary OA load of the patient.

In routine practice for PD, different solutions with various compositions of OA, electrolytes and buffers are used. The concentration of the OA is the main driver of ultrafiltration (UF). The biggest problem today is to choose the right dialysate OA concentration, fill volume and dwell time to target the individual patient's needs. Due to a feedback control system with quasi-continuous input of hydration status measured by body composition monitor (BCM) or known dry weight concepts, a target hydration status or body weight defined by the nephrologist and the ultrafiltration volume (UFV) response of every treatment, the treatment could be optimized for the individual patient without trial and error prescriptions. The feedback controller may cause an oscillation around the target hydration status to solve the problem of overhydration and dehydration in PD treatment. The treatment schedule created from this concept may also be sufficient to remove enough uremic toxins, because this is less complicated to achieve in dialysis treatment today and could be tested by established quality assurance tests (e.g., peritoneal equilibration test, PET).

Figure 15:
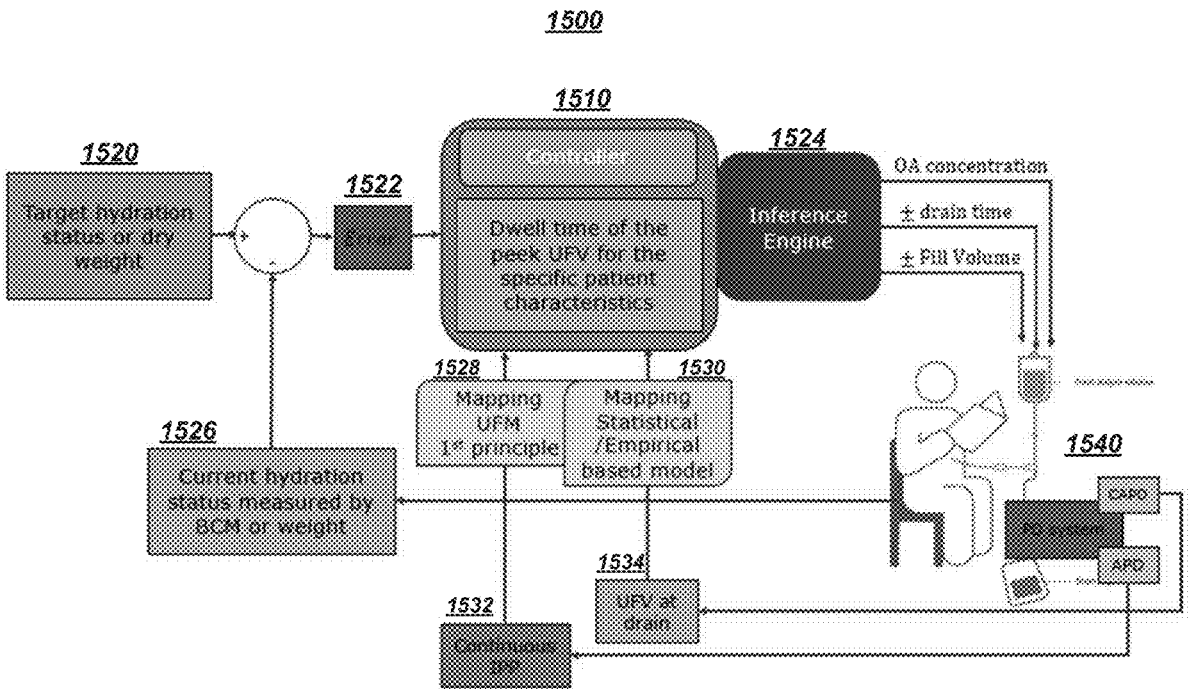
FIG. 15 illustrates a feedback control system in accordance with the present disclosure.

FIG. 15 depicts a feedback control system in accordance with the present disclosure. As shown in FIG. 15, a target hydration status 1520 may be determined for a patient, e.g., set by a healthcare professional and input into system 1500. For a regular treatment, the patient or healthcare professional may need to measure the patient hydration status or body weight 1526 various times, e.g., at the start of every cycle. The resulting deviation (error) 1522 of every BCM measurement 1526 (or body weight and dry weight) from the target hydration status 1520 may be calculated and saved to a vector. This vector may be used to calculate the control signal for the feedback control system 1510. A non-limiting example of a controller may be or may include a PID-controller.

An input may include a continuous IPP measurement 1532 during APD or the drained dialysate volume (CAPD) to get information about the patient specific UF behavior and the peak time of the peritoneal cavity volume. In some embodiments, the IPP measurement 1532 may be processed via a mapping UFM first principal process, e.g., the same or similar to processes described in the 210062 Application. In various embodiments, the input may include UFV at drain 1534, for example, as part of a mapping statistical/empirical based model, such as a PD optimization process according to some embodiments. The input may be determined and/or provided at various times, including, e.g., every cycle.

With the data generated by the controller 1510, inference engine 1524 changes the treatment conditions for the following cycle dependent on the control signal. For the timing of the drain, the shortest dwell time may be set at the peak of the UFV in the peritoneal cavity to also achieve sufficient clearance of toxins. The fill volume should not be so high that the patient may, with the additional volume in the cavity resulting from UF, feel pain or other unwanted effects. Dependent on the residual renal function of the patient, the lowest OA concentration possible may be used to keep the patient in the range of euvolemic hydration, e.g., to avoid very long dwells and unnecessary glucose absorption and loading of the patient.

In some embodiments using a dialysate mixing system were to produce the PD fluid with varying OA concentration for the patient, a further control variable with high impact to the UF performance may be used.

Figure 16:
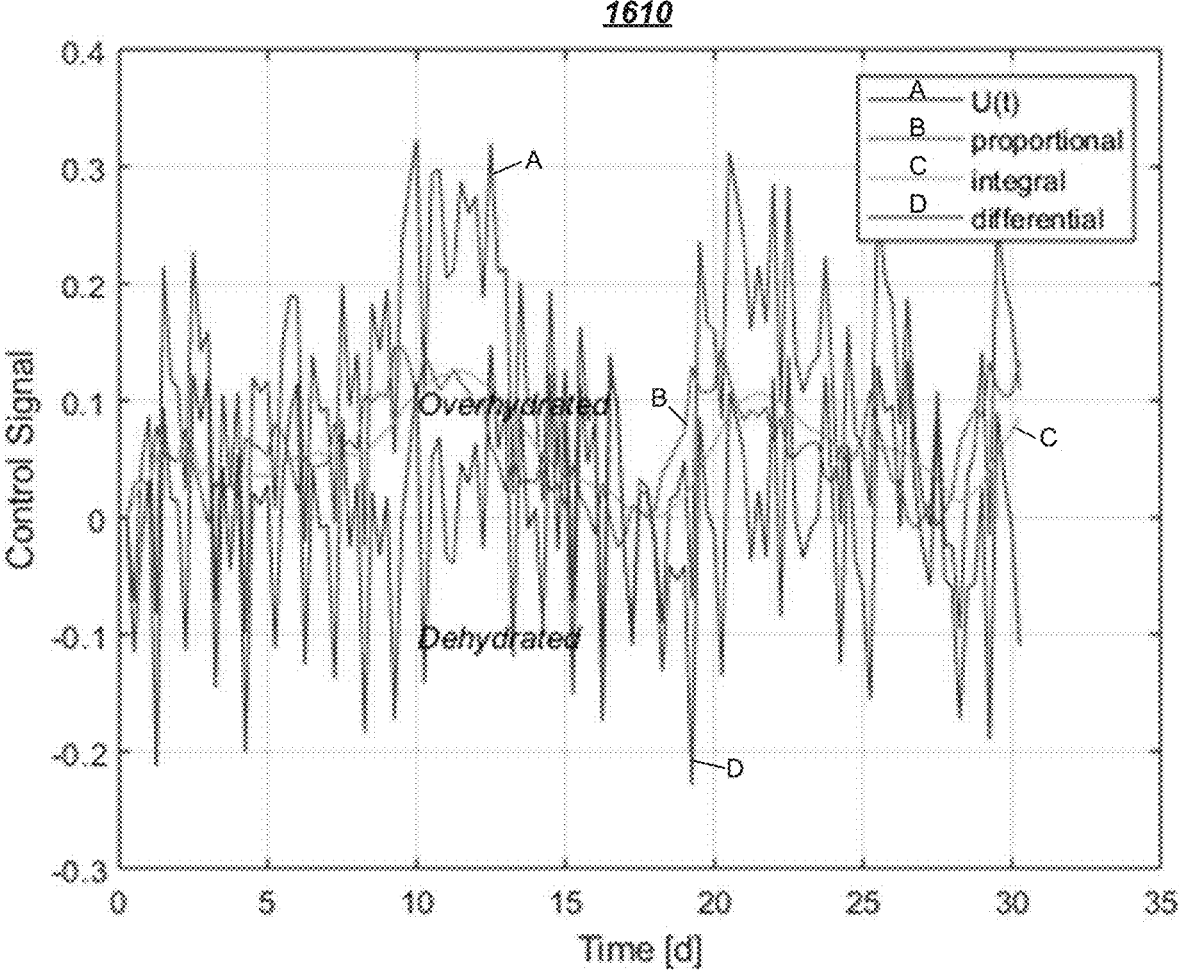
FIG. 16 depicts a graph of a control signal associated with a control system in accordance with the present disclosure.

Referring to FIG. 16, therein is depicted graph 1610 of a control signal. For example, a control signal U(t) is shown over 30 days, with a signal above 0 indicating the patient is overhydrated and a signal below 0 indicating the patient is dehydrated. The control signal may be calculated from the deviation between target hydration status and measured hydration status for the individual patient according to the following Equation (13):

$$\text{Error}(t) = \text{Measured Hydration}(t) - \text{Target Hydration}.$$

Equation (13) calculates the deviation of the measured status from the target hydration status or weight. From this the information, whether the patient is dehydrated with a negative error or overhydrated with a positive error may be derived. The calculated error is then added to a vector which includes calculated errors from some or all previous cycles, such as depicted in the following error vector:

$$\overrightarrow{\text{Error}} = \begin{bmatrix} \text{Error}(1) \\ \text{Error}(2) \\ \text{Error}(3) \\ \dots \\ \text{Error}(t) \end{bmatrix}$$

The variable (t) is related to the last or most actual measured and calculated error.

The following Equation (14) may be used to determine the control signal U(t) for a controller, such as a PID controller:

$$U(t) = w_P * \text{Error}(t) + w_I * \int_{t-x}^{t} \text{Error}(t')dt' + w_D * \frac{dError(t)}{dt}.$$

In some embodiments, only part of the PID controller may be required, such that only the proportional, integral, or differential part, or a combination thereof, are used. Equations (15)-(17) depict the equations for the proportional part, integral part, and differential part, respectively:

$$U(t) = w_P * \text{Error}(t)$$

$$U(t) = w_I * \int_{t-x}^{t} \text{Error}(t')dt',$$

$$U(t) = w_D * \frac{dError(t)}{dt}.$$

For the integral part, the x in Equation (15) specifies how far the integral part should consider the history of treatment. For example, if the value for x is set to 10, only the last 10 cycles are used to calculate the integral.

The signal U(t) may be fed into an inference engine or expert system (or computational model according to some embodiments), which may change parameters, such as the dwell time, fill volume and PDF OA concentration dependent on predefined conditions, the knowledge base, the other data available from previous cycles, and/or the like.

The following provides an example of a logical rule application for the specific problem of hydration control on PD:

1. If the OA concentration is not sufficient to protect the patient from overhydration, the next higher available OA concentration may be used; conversely, a lower OA concentration may be used if the patient could not be protected from dehydration. Continue with the same OA concentration if the UFV is sufficient to keep the patient in a range near the target hydration status.
2. The maximum and the minimum fill volume may be defined, and the step size of varying the fill volume, dependent on the patient specific inputs. If the patient is dehydrated decrease the fill volume and vice versa.
3. The minimum and maximum dwell time may be defined, and the step size of varying the dwell time, dependent on the patient specific inputs. If the patient is overhydrated decrease the dwell time and vice versa.
4. Minimum dwell time may be at the peak of the UFV.

In some embodiments, a hydration control—expert system may include a user interface, such as a mobile app (medical software application) or the interface of the PD device used by the patient (cycler, etc.). The query may be the patients input data, such as daily schedule (work, exercise, etc.). A patient specific knowledge base may include patient information, such as hydration status measurement, target hydration status set by the nephrologist, used OA concentration, fill volume, dwell time of the last cycle, and/or other calculated or simulated/modelled data from historical treatment data. In one example, the data which are constant for a longer period of time may be transferred to the knowledge base with the referring rules and conditions applied from the inference engine and the expert knowledge to further improve the individualized treatment.

An end user may put in the relevant information to the user interface at the start of the next cycle, or connected measuring devices, such as weight scales, pressure transducers and BCM may automatically provide information to the system. All data collected may be saved to a database. After all relevant data are provided to the system, the system may run through a decision tree in the inference engine, with the related knowledge base rules applied. If the system ends at a chance node, different endpoint nodes with different treatment options for the patient may be displayed with reasonable explanations for each and the patient or healthcare professional could select the cycle conditions which best fits the needs of the patient. These procedures may be repeated at various intervals, such as the start of every cycle, each treatment, etc., to automatically revise the treatment schedule by the expert system to achieve a target hydration status.

Expert knowledge and other related information may be stored inside the knowledge base, which may be used as a basis for patient treatment decisions. The overall knowledge may be general for all patients and may be used in models that can represent the UF mechanism in the easiest way possible, but because of the different needs of the patients dependent on residual renal function and many other influences (diabetes, body weight, patient's life style etc.), the treatment needs may be individualized for each patient.

The models used may produce knowledge about the patient's specific transport characteristic by continuous measurement of IPP over the dwell time, PDF OA concentration and start fill volume, if a cycler is used, and/or the like. For this first possibility a simplified first principles model may be used, such as described in the 210062 Application. If the patient uses CAPD, which would be manually performed without measurement of IPP continuously, a statistical model approach may be used, such as a PD optimization process according to some embodiments. For example, such models may use the drain volume to calculate the UFV ($t_{dwell}$), the start fill volume and PDF OA concentration to generate knowledge about the individual patient.

The models may predict after sufficient data acquisition, for example, how much UFV at the following cycle for the specific patient could be achieved by given initial conditions (e.g., % PDF, Fill Volume, dwell time). This process may result in a more flexible treatment for the patient because the patient can decide which dwell time to use by different options on the system user interface.

Figure 17:
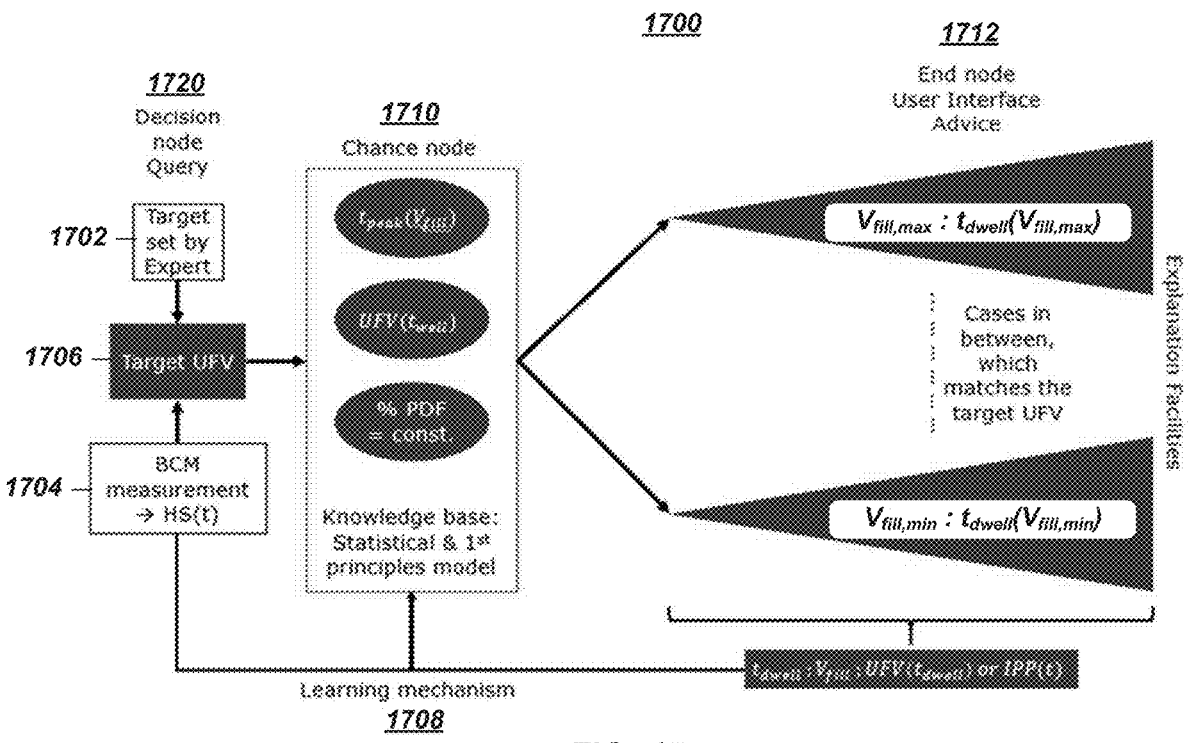
FIG. 17 depicts an illustrative expert system in accordance with the present disclosure.

FIG. 17 depicts an illustrative expert system according to some embodiments. At the beginning of a PD treatment, the nephrologist or other healthcare professional may set 1702 the hydration status target of the treatment. The input for the system 1700 may be the target 1706 identified by the expert and the measured hydration status 1704 by BCM or dry weight methods. In some embodiments, after all relevant data are feed to the system 1700, the system 1700 runs through the decision tree in the inference engine, with the related knowledge base rules applied. If the system 1700 includes a chance node 1710, different endpoint nodes 1712 with different treatment options for the patient could be displayed, e.g., with reasonable explanations for each and the patient or healthcare professional could select the cycle conditions which best fits the patient's individual needs As shown in FIG. 17, from the decision node query 1720, a target UFV for the following cycle may be calculated. Per forward chaining, the system 1700 may calculate from measured treatment data history, e.g., with initial conditions to match the goals. The knowledge base and the models included to generate expert knowledge for the specific patient deliver, in combination with an inference engine, suitable treatment options. The patient may select a dwell time and/or other treatment parameters and the initial conditions for the next cycle are chosen by the system 1700.

After performing the cycle, the initial conditions may be saved to the knowledge database, dependent on the prediction accuracy of the models. For an error bigger than a predefined deviation from the measured UFV, the data of the model calculations may be neglected and, in some embodiments, a message to the patient to contact a healthcare professional may be provided because of the possibility of peritonitis and membrane changes (reference to statistical based patent). If the prediction matches the measured UFV to a certain range/threshold/etc., the dataset generated from the cycle may be saved to the database and may be used to optimize the following cycles. In addition, a trend may be generated to determine how the hydration status and other patient specific data change in the course of treatment could be used as case study results to further improve the individualized treatment.

Figure 18A:
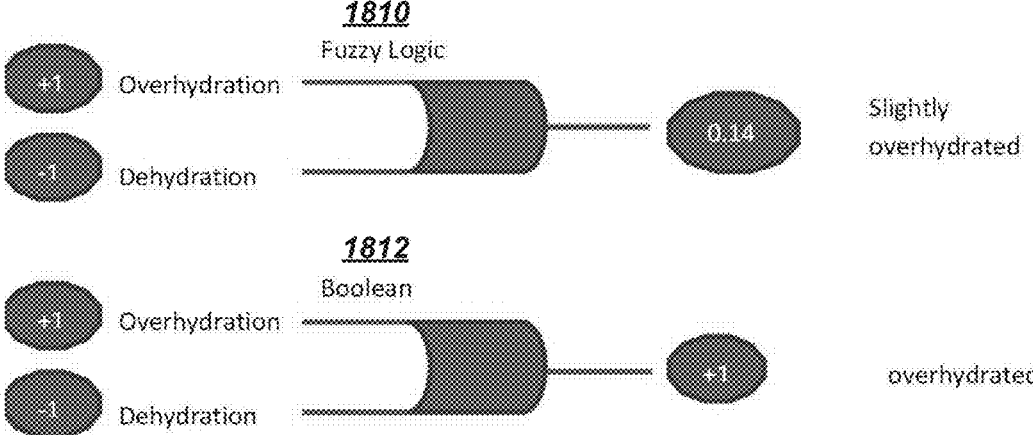
FIG. 18A depicts an illustrative schematic diagram comparing a fuzzy logic structure with a Boolean structure in accordance with the present disclosure.

In some embodiments, fuzzy logic principals may be used in combination with an inference engine to allow for the definition of specific rules to change the treatment conditions dependent on the real hydration status deviation from the target hydration of the patient compared to a controller (e.g., a PID controller) which uses the information that the patient is over- or de-hydrated (e.g., a Boolean value). FIG. 18A depicts an illustrative schematic diagram comparing a fuzzy logic structure 1810 with a Boolean structure 1812.

Figure 18B:
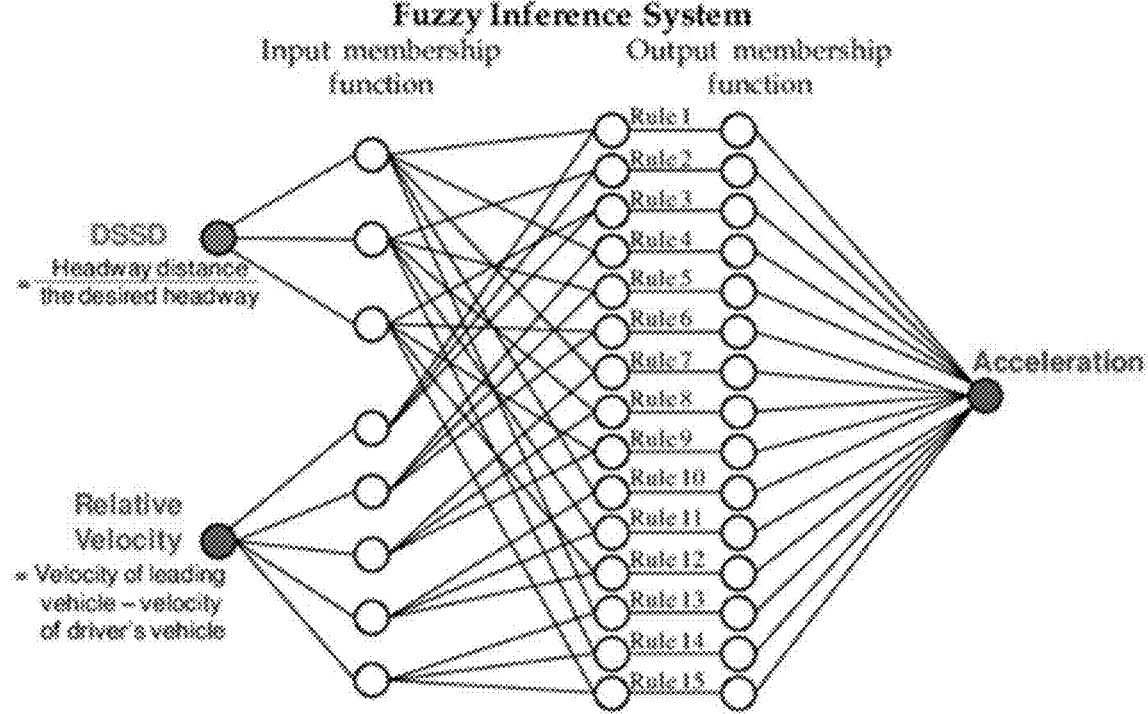
FIG. 18B depicts an illustrative schematic diagram of an example fuzzy interference system in accordance with the present disclosure.

In some embodiments, a fuzzy inference system may be used based on previous treatment conditions and further information to vary the treatment conditions according to rules applied specifically to further minimize fluctuations around the target hydration status. FIG. 18B depicts an illustrative schematic diagram of an example fuzzy interference system. In various embodiments, a Kalman filter may be used to reduce the need of regular evaluations of the actual hydration status to estimate the day-to-day hydration status of the specific patient by further inputs which may be available through various means.

Figure 19:
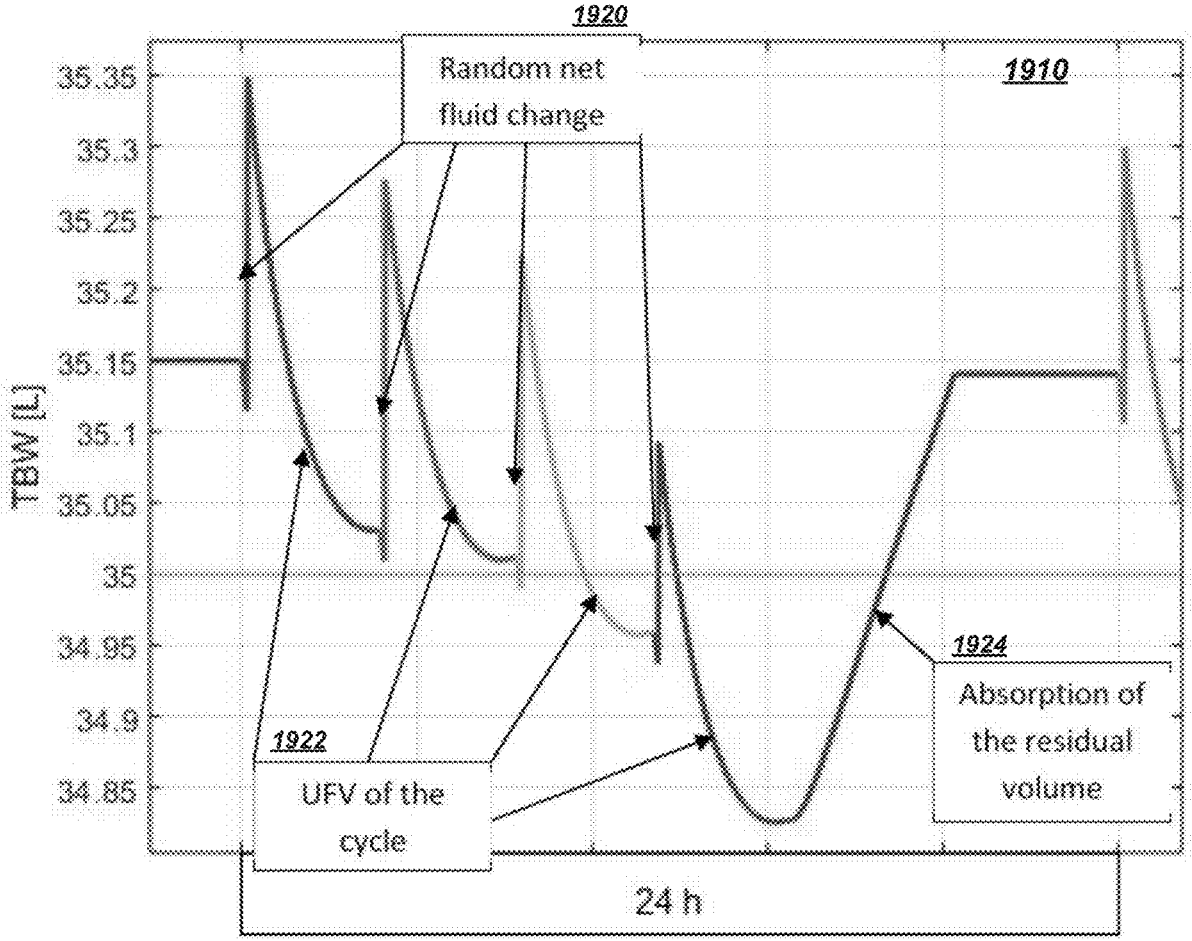
FIG. 19 depicts a graph schematically representing total body water (TBW) for a patient over a twenty-four hour period.

FIG. 19 depicts a graph 1910 schematically representing total body water (TBW) for a patient over a twenty-four hour period. At the start of each cycle the TBW is measured according to various methods. A random fluid change 1920 is included at the beginning of each cycle to compensate fluid intake, urinary output, etc. Then after infusing the dialysate, UF occurs removing volume 1922 from the TBW. After the last cycle of the day, the residual volume in the cavity gets reabsorbed 1924 by the body, and the process starts again for the next twenty-four hour cycle.

Accordingly, FIG. 19 shows data schematically representing how TBW is changing by simulation of the PD treatment over a time span of days. At the start of every treatment cycle, a random fluid volume may be added to the TBW (between −0.05 and 0.4 L) to account for the fluid intake by drinking and eating, but also for the fluid excreted by the kidneys via urinary output and the insensible losses. A non-limiting example of determining a random net fluid change may be according to the following: Random net fluid change=drinking+eating−urinary output−insensible losses.

For simulation purposes this should be sufficient, because the TBW measurement to get hydration status information would be only performed at the start of the cycle. After this measurement the cavity gets filled with dialysate and due to the osmotic pressure gradient through the peritoneal membrane, water from the body of the patient is transported by UF to the cavity. After the dwell time, draining of the cavity volume including the UFV may be performed, resulting in a net decrease of the TBW. After the last cycle of the day, in this simulation the patient has a dry phase overnight, such that after the last drain of the day no additional fill would be performed. The residual volume, which remains in the peritoneal cavity after the drain gets reabsorbed by the lymph system and trough the peritoneal cavity after some time, until the cavity is nearly empty again.

Figure 20:
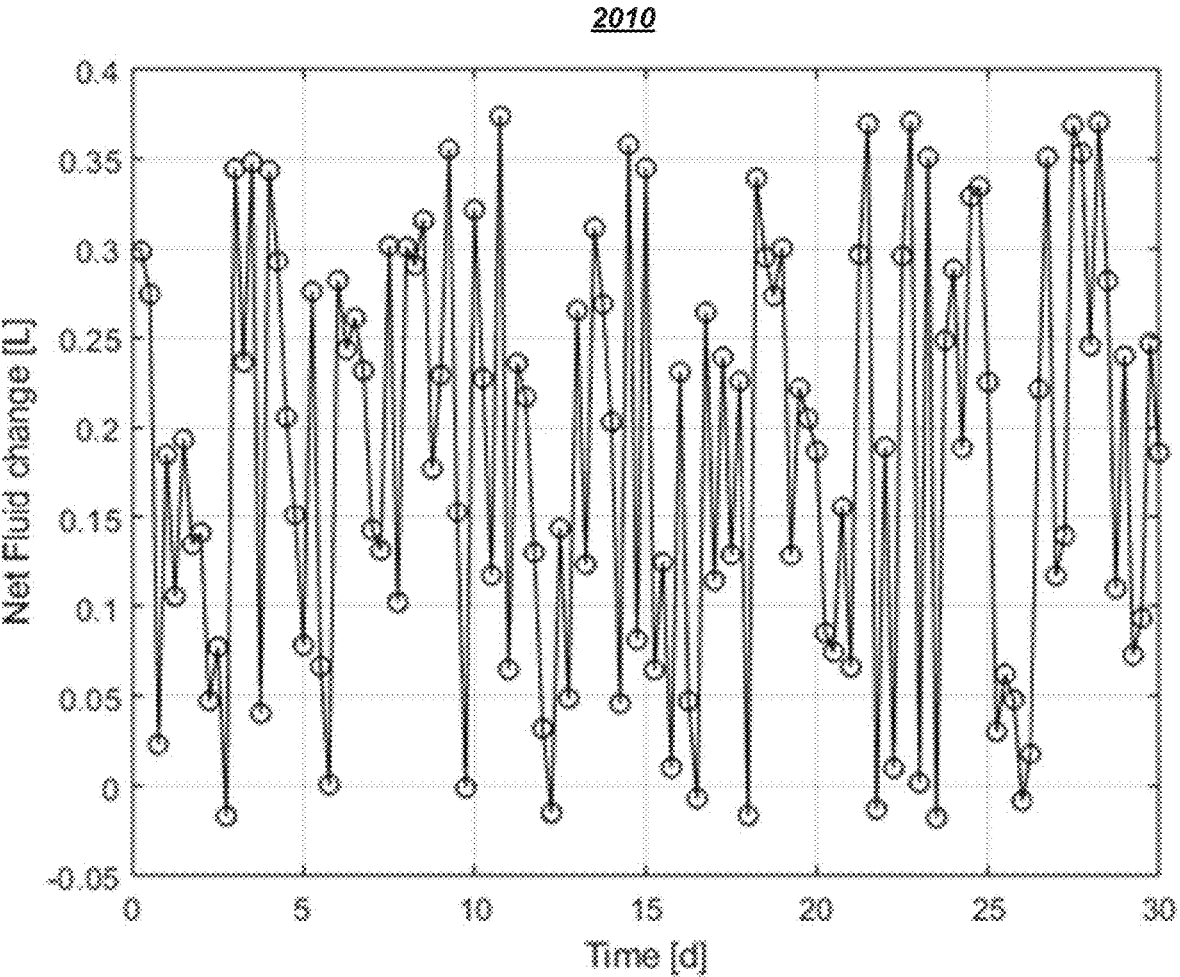
FIG. 20 depicts a graph of net fluid change over a time period in accordance with the present disclosure.

As a result of the net fluid intake, TBW will change. FIG. 20 depicts graph 2010 of the net fluid change over a time period of thirty hours. In addition, the reabsorption of the residual cavity volume, after the drain, increases the amount of TBW. If the treatment conditions are, for example, four cycles per day, which is equivalent to the number of hydration measurements according to the simulation of FIG. 19, the net fluid intake over the whole day causes the TBW volume to increase, which needs to be compensated by the PD treatment cycles.

Figure 21:
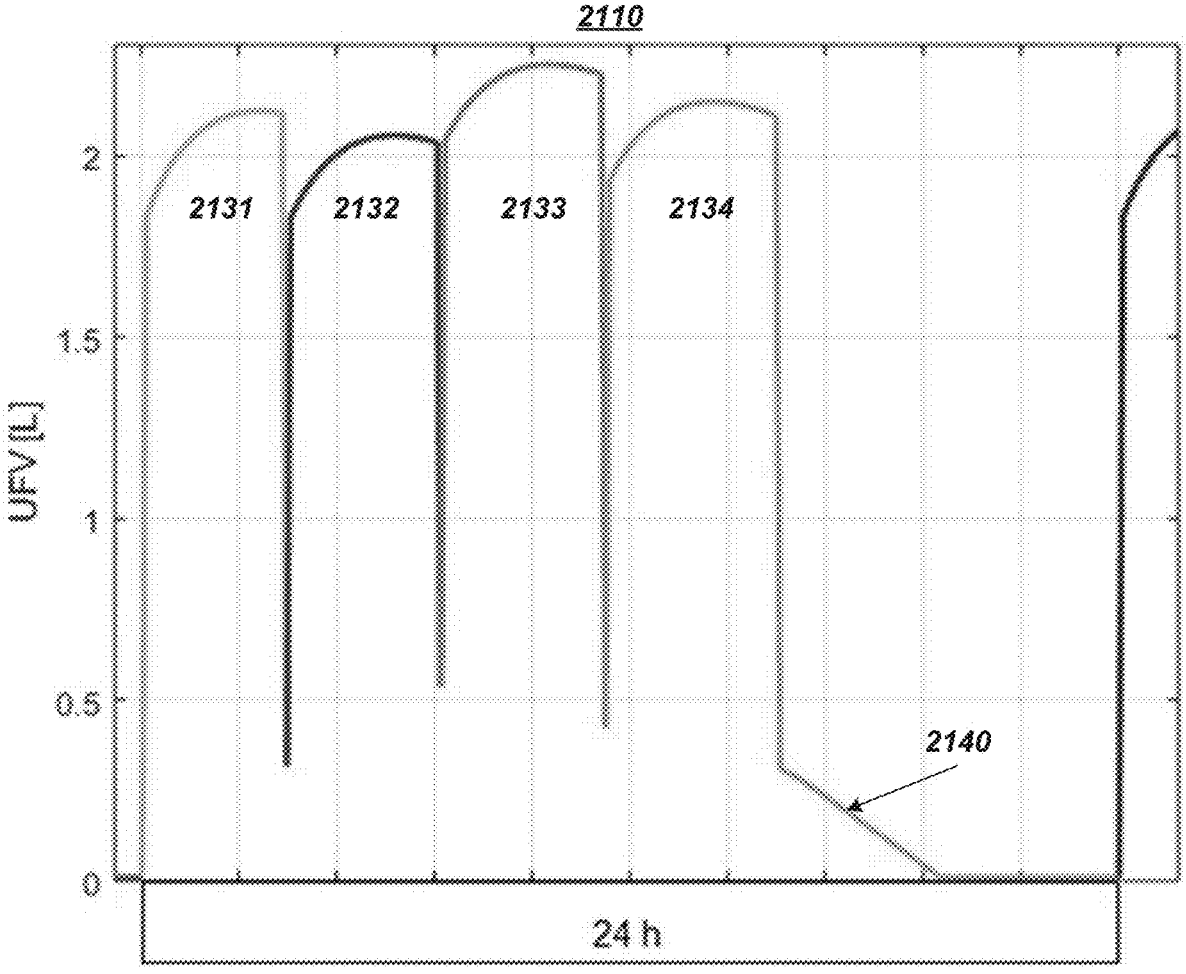
FIG. 21 depicts a graph of UFV over a time period during PD cycles in accordance with the present disclosure.

FIG. 21 depicts graph 2110 of UFV over a time period of twenty four hours during four PD cycles (2131-2134). Assuming that during the dry phase overnight, the cavity is empty due to reabsorption, the first cycle of the day starts with filling the cavity with a dialysate volume (e.g., between 1.75-2.25 liters) dependent on the hydration status measured for the patient. After the fill phase at the beginning of the cycle, the dwell phase follows with different time spans depending on the hydration status measurement calculations, followed by the drain. If higher UFV at the drain is needed, the system will change the fill volume, dwell time, and/or PDF composition and vice versa. This process may be repeated over the day (e.g., 4 times (cycles 2131-2134)). After the last drain of the day, during the dry phase, the residual volume gets reabsorbed 2141.

Figure 22:
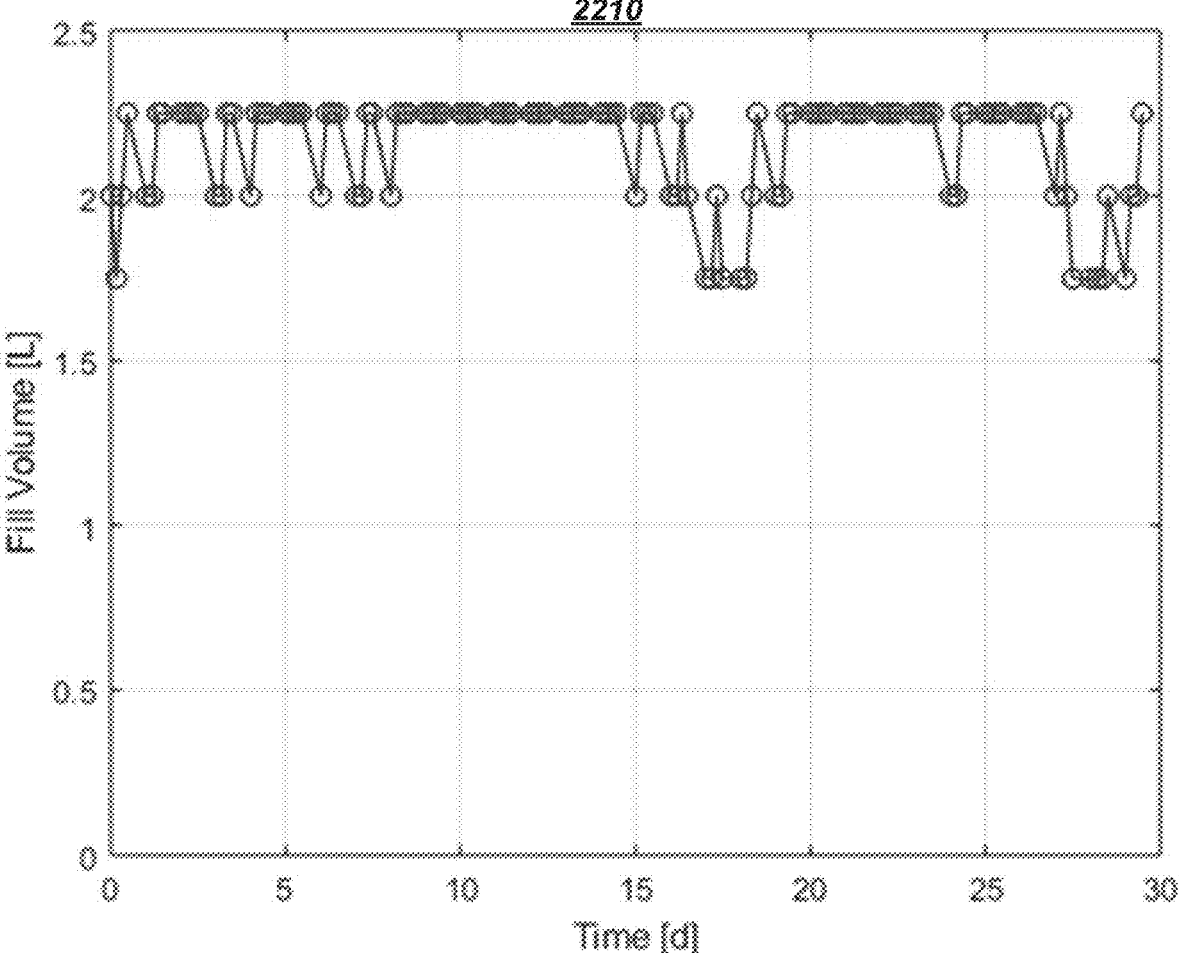
FIG. 22 depicts a graph of a variation of fill volume in accordance with the present disclosure.

To control the fill volume and dwell time, a control system combined with an inference engine configured according to some embodiments may be used. FIG. 22 depicts graph 2210 of the variation of the fill volume in 0.25 L steps between 1.75 and 2.25 L via an inference engine based on a control system knowledge base according to some embodiments.

Figure 23:
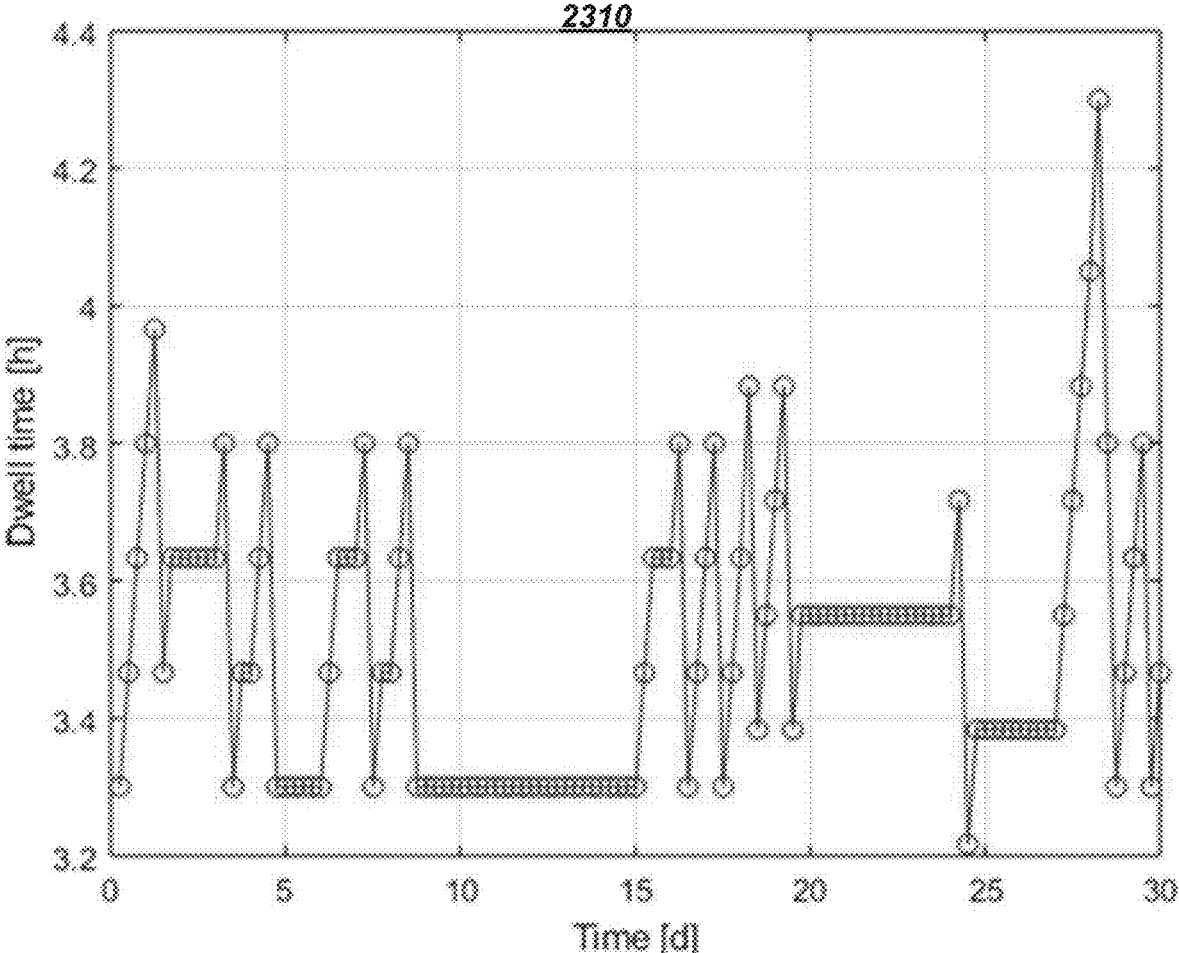
FIG. 23 depicts a graph of the dwell time changed by an inference engine in accordance with the present disclosure.

In some embodiments, dependent on the control signal, the time of the dwell and the fill volume may be in a predefined step size elongated or shortened until it reaches a maximum dwell length defined or the peak time as shortest dwell time and a maximum and minimum fill volumes based on logical rules of the knowledge base applied by the inference engine configured according to some embodiments. FIG. 23 depicts graph 2310 depicting the dwell time changed by an inference engine according to some embodiments between 3 and 5 hours in a predefined step size. In various embodiments, if the time gets longer, the time steps may be selected for the simulation depending on the patient history data and knowledge base information.

Figure 24:
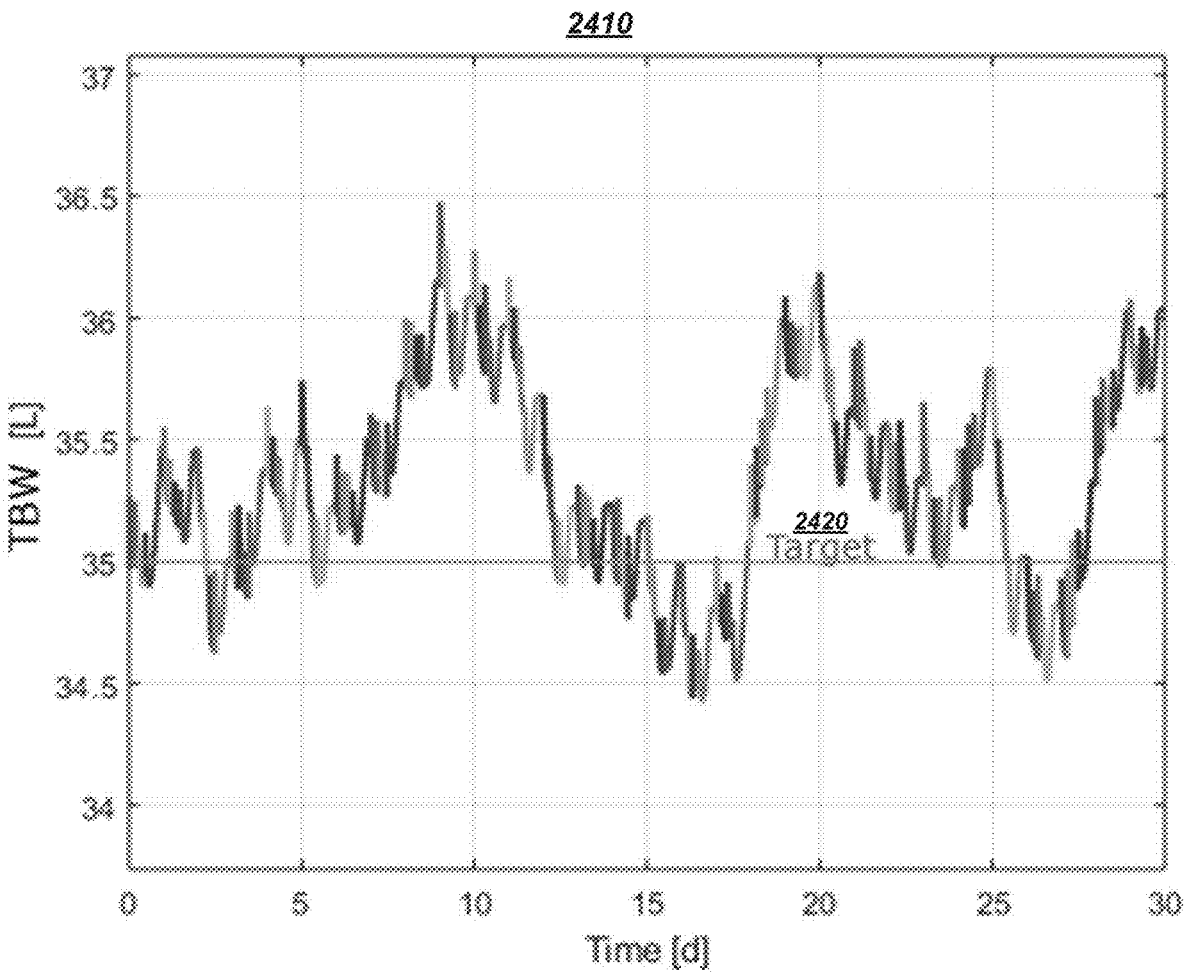
FIGS. 24 and 25 depict graphs of simulation results in accordance with the present disclosure.

FIG. 24 depicts graph 2410 of a simulation according to various embodiments. The simulation represented in graph 2410 indicates the fluctuation around a target hydration status 2420 of a patient. The hydration status is represented by TBW for simulation purposes.

Figure 25:
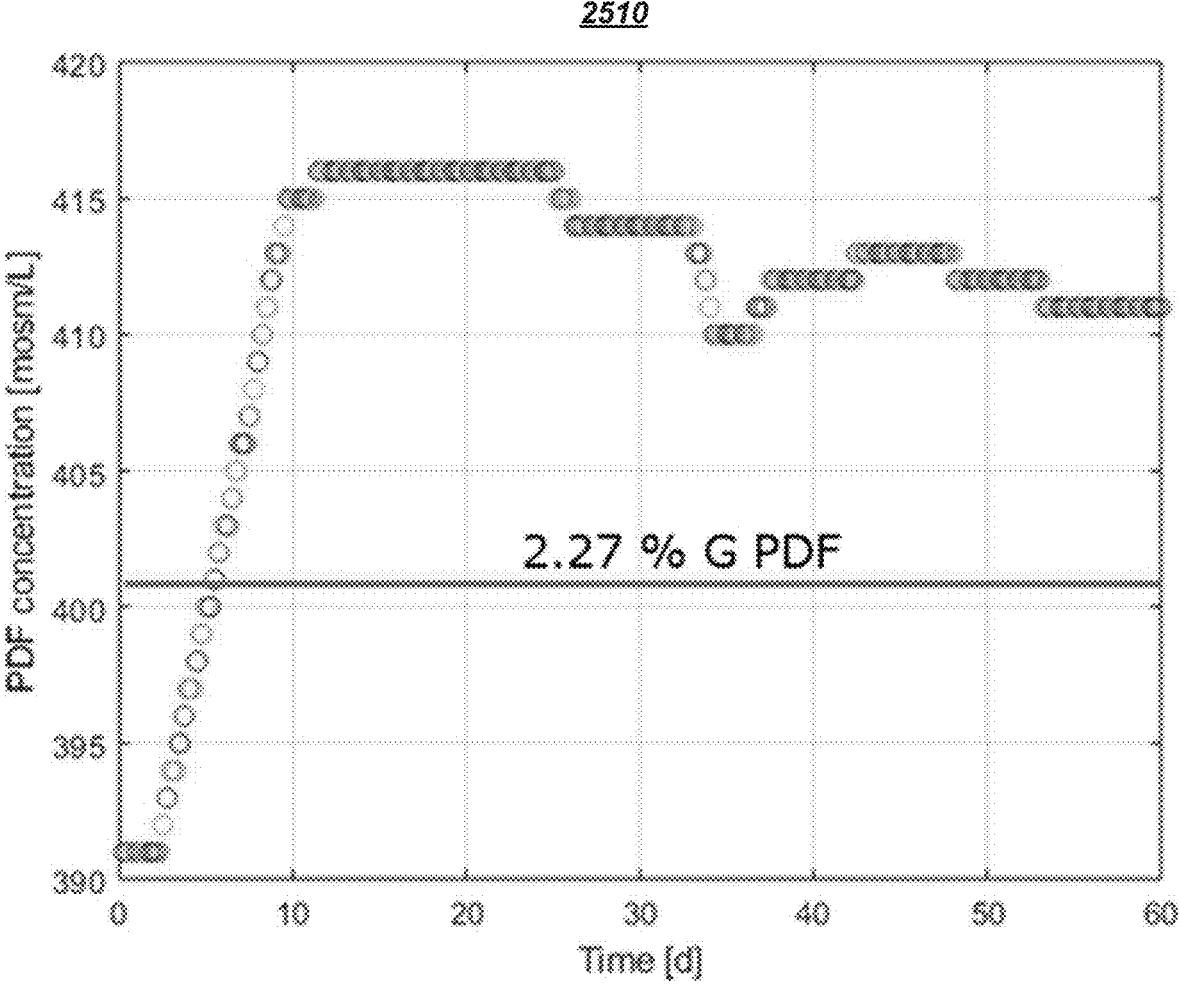

FIG. 25 depicts graph 2510 of a simulation according to various embodiments of the variation of PDF osmolarity by a control system in combination with an on-the-fly mixing system. The initial osmolarity results from the osmolarity of the matrix (ca. 275 mosm/l) plus the OA osmolarity. For the simulation of graph 2510, the treatment started with a low OA concentration, during the first 10 days, the OA concentration was increased by the control system to compensate for insufficient UFV. After reaching the osmolarity, which is sufficient to protect the patient from overhydration, the control system further modifies the OA input to the patient to minimize glucose absorption, get sufficient clearance and UFV to keep the patient on a healthy hydration status.

PD treatment processes according to some embodiments may provide multiple technological advantages over existing systems. The technological advantages may provide improved patient experiences and outcomes. For example, patient quality of life would be improved by flexible treatment scheduling, less visits to the clinic, and/or less bag combinations. These benefits result from the quasi-continuous treatment control, which accounts for changes in the treatment schedule dependent on the patient's lifestyle automatically without needed clinic visits to revise the prescription. In another example, only one type of OA concentration of the PDF bag may be required because only the lowest OA glucose concentration possible to control the patient's hydration status may be used.

Because of the usage of the lowest OA concentration the exposure to glucose is minimized, which is associated with decreased or even eliminated peritoneal membrane changes and damage, which would help avoid UF failure and other complications.

In addition, the operational aspects of PD may be improved because the costs are reduced if the patient remains longer on PD instead of requiring hemodialysis (which is more expensive). Further costs could be reduced due to less visits to the clinic because of wasteful trial and error (blind) prescriptions. Systems and processes according to some embodiments may be combined with continuous IPP measurement to also optimize APD and use objective adapted APD prescriptions (e.g., with first principles model patent). In addition, a CAPD treatment may use systems and processes according to some embodiments approach in combination with suitable models (e.g., statistical models according to various embodiments).

Figure 26:
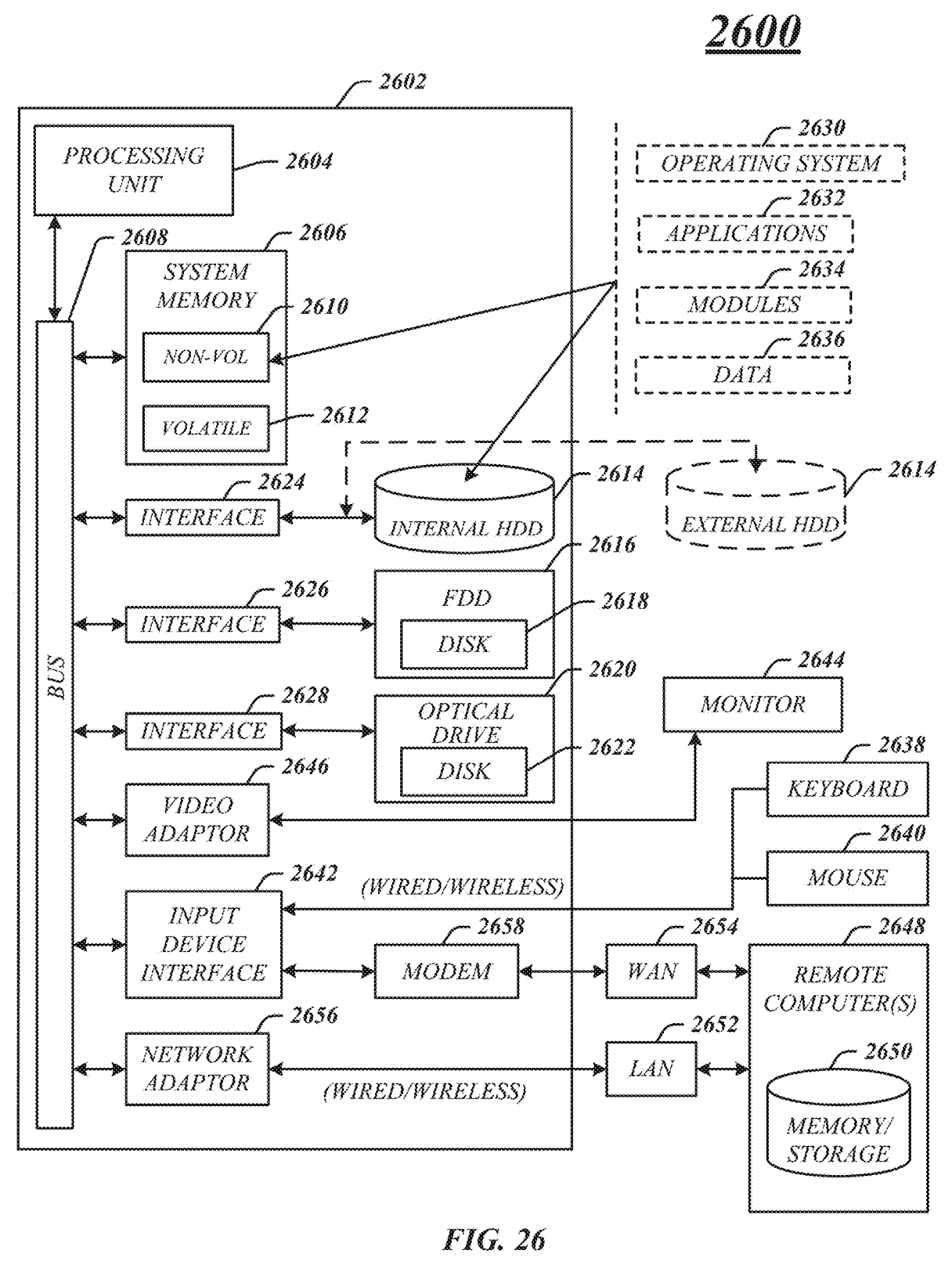

FIG. 26 illustrates an embodiment of an exemplary computing architecture 2600 suitable for implementing various embodiments as previously described. In various embodiments, the computing architecture 2600 may comprise or be implemented as part of an electronic device. In some embodiments, the computing architecture 2600 may be representative, for example, of computing device 260. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 2600. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 2600 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 2600.

As shown in FIG. 26, the computing architecture 2600 comprises a processing unit 2604, a system memory 2606 and a system bus 2608. The processing unit 2604 may be a commercially available processor and may include dual microprocessors, multi-core processors, and other multiprocessor architectures.

The system bus 2608 provides an interface for system components including, but not limited to, the system memory 2606 to the processing unit 2604. The system bus 2608 can be any of several types of bus structure that may further interconnect to a memory bus (with or without a memory controller), a peripheral bus, and a local bus using any of a variety of commercially available bus architectures. Interface adapters may connect to the system bus 2608 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 2606 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 26, the system memory 2606 can include non-volatile memory 2610 and/or volatile memory 2612. A basic input/output system (BIOS) can be stored in the non-volatile memory 2610.

The computer 2602 may include various types of computer-readable storage media in the form of one or more lower speed memory units, including an internal (or external) hard disk drive (HDD) 2614, a magnetic floppy disk drive (FDD) 2616 to read from or write to a removable magnetic disk 2611, and an optical disk drive 2620 to read from or write to a removable optical disk 2622 (e.g., a CD-ROM or DVD). The HDD 2614, FDD 2616 and optical disk drive 2620 can be connected to the system bus 2608 by a HDD interface 2624, an FDD interface 2626 and an optical drive interface 2628, respectively. The HDD interface 2624 for external drive implementations can include at least one or both of Universal Serial Bus (USB) and IEEE 2614 interface technologies.

The drives and associated computer-readable media provide volatile and/or nonvolatile storage of data, data structures, computer-executable instructions, and so forth. For example, a number of program modules can be stored in the drives and memory units 2610, 2612, including an operating system 2630, one or more application programs 2632, other program modules 2634, and program data 2636. In one embodiment, the one or more application programs 2632, other program modules 2634, and program data 2636 can include, for example, the various applications and/or components of computing device 2600.

A user can enter commands and information into the computer 2602 through one or more wired/wireless input devices, for example, a keyboard 2638 and a pointing device, such as a mouse 2640. These and other input devices are often connected to the processing unit 2604 through an input device interface 2642 that is coupled to the system bus 2608, but can be connected by other interfaces.

A monitor 2644 or other type of display device is also connected to the system bus 2608 via an interface, such as a video adaptor 2646. The monitor 2644 may be internal or external to the computer 2602. In addition to the monitor 2644, a computer typically includes other peripheral output devices, such as speakers, printers, and so forth.

The computer 2602 may operate in a networked environment using logical connections via wired and/or wireless communications to one or more remote computers, such as a remote computer 2648. The remote computer 2648 can be a workstation, a server computer, a router, a personal computer, portable computer, microprocessor-based entertainment appliance, a peer device or other common network node, and typically includes many or all of the elements described relative to the computer 2602, although, for purposes of brevity, only a memory/storage device 2650 is illustrated. The logical connections depicted include wired/wireless connectivity to a local area network (LAN) 2652 and/or larger networks, for example, a wide area network (WAN) 2654. Such LAN and WAN networking environments are commonplace in offices and companies, and facilitate enterprise-wide computer networks, such as intranets, all of which may connect to a global communications network, for example, the Internet.

The computer 2602 is operable to communicate with wired and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Figure 27:
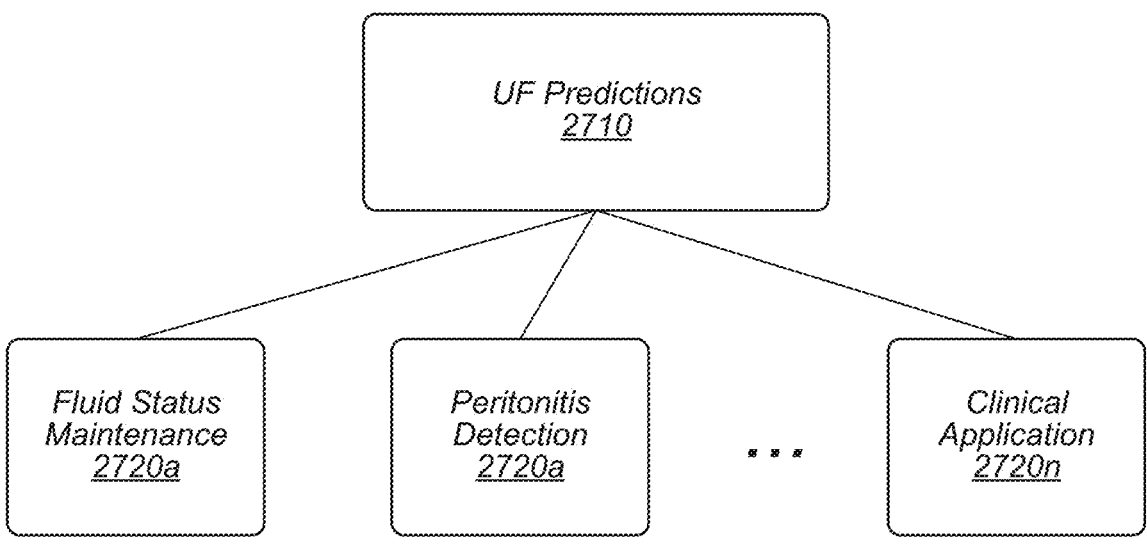
FIG. 27 depicts clinical applications associated with UFV predictions in accordance with the present disclosure.

FIG. 27 depicts clinical applications associated with UFV predictions. UFV predictions 2710 may be determined according to various processes, including statistical or first principal techniques. One or more UFV predictions 2710 may then be used in various clinical applications 2720a-n. Non-limiting examples of clinical applications 2720a-n may include fluid status maintenance 2720a and peritonitis detection (or prediction) 2720b. Accordingly, UFV predictions 2710 may be applied in various techniques of patient treatment.

Regarding the maintenance of hydration status of a patient, the TBW of a subject may undergo diurnal variation, for example, due to ingestion of food and water, urinary output, subject activity, and/or the like. This leads to small random variation in TBW about a nominal value of TBW that the normal kidney function serves to maintain. In kidney failure, more of the fluid that is ingested accumulates in body tissues as excess fluid. Dialysis treatment, or more specifically the process of ultrafiltration, serves to remove this excess fluid.

Figure 28:
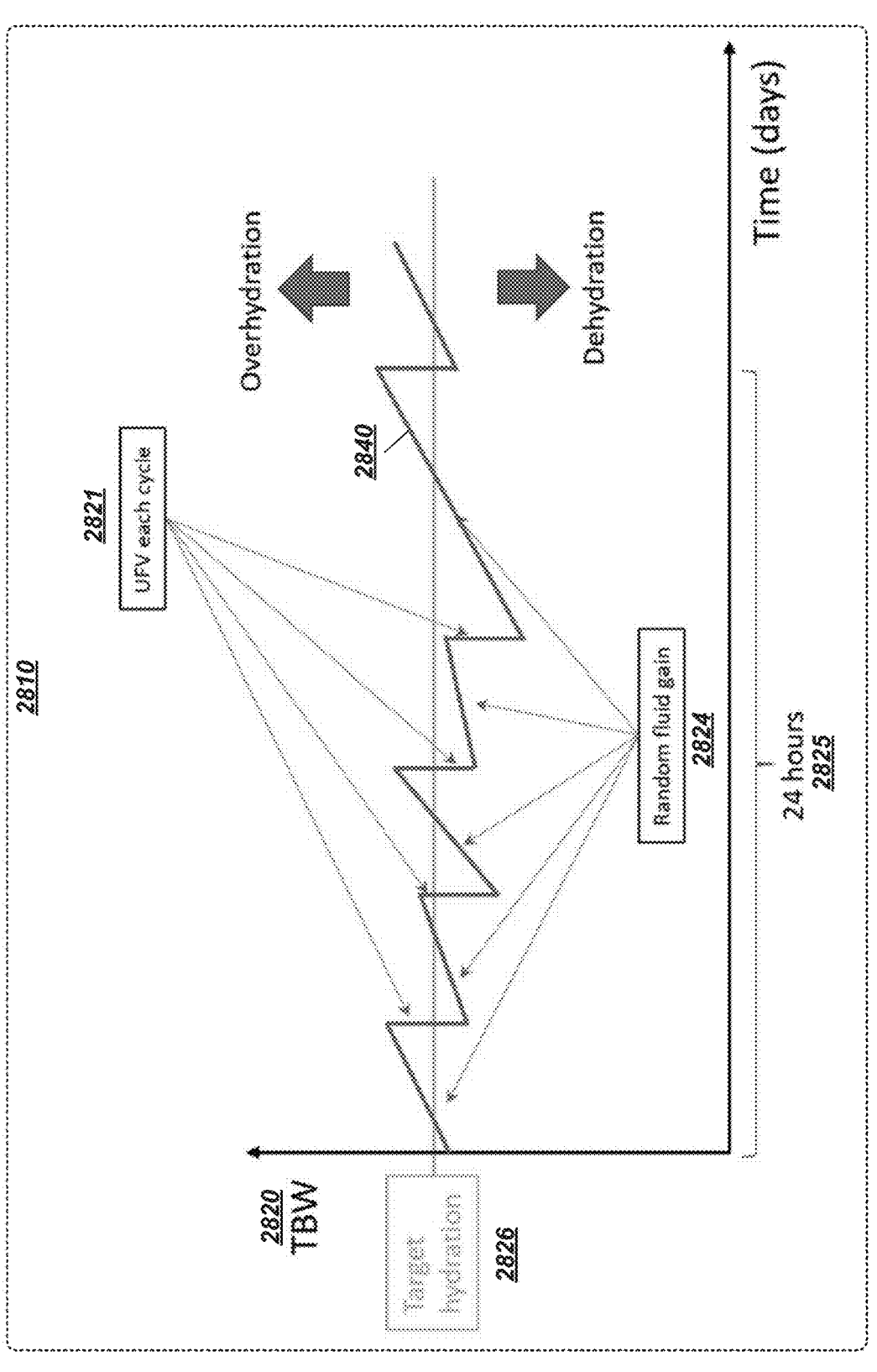
FIG. 28 depicts a graph of variation in total body water (TBW) over a time period in accordance with the present disclosure.

FIG. 28 depicts graph 2810 of variation in TBW 2820 over a 24-hour period 2825 and removal of excess fluid accumulation by ultrafiltration. Graph 2810 depicts a TBW plot 2840 about a target hydration status 2826. TBW plot 2840 is modified by random fluid gain 2824 and UFV 2821 for each cycle of PD.

An essential basis for any fluid removal strategy is the identification of a hydration target (e.g., 2826 of FIG. 28) for the individual patient. Essentially, the target reflects the hydration that should be achieved if the kidney were to work normally, considering adjustments necessary to mitigate any deleterious effects of comorbidity. The control of ultrafiltration requires both the hydration target and suitable measurements of the patient's hydration status. Multiple measurements of hydration status over several days may be considered. These measurements may be averaged (to compensate for measurement errors) and used to track typical variation in hydration status. The measurement of hydration status may be achieved via a number of possible established methods. Hydration status may be measured at suitable intervals e.g., daily, so that the control loop can compensate for variations in hydration status on a treatment-by-treatment basis. The difference between the hydration target and the current hydration status is the error or the signal that is fed into a controller configured according to some embodiments.

FIG. 29 illustrates an exemplary operating environment in accordance with the present disclosure. More specifically, FIG. 29 depicts a process that uses an inference engine 2901 to determine dose variables 2903. Inference engine 2901 may include a UF prediction module 2940 having a dose variable optimizer 2941. In some embodiments, dose variable optimizer model 2941 may receive a model parameter set 2960 and patient and/or unknown information 2914 as input. Dose variable optimizer model 2941 may operate to adapt dose variables 2903 of a prescription 2902 to minimize an error 2916 between a predicted UFV 2910 and a target UFV 2938. Prescription 2902 may be used for dialysis treatment of patient 2950. Patient hydration statuses may be measured 2924, for instance, daily, to determine a hydration status 2923. A hydration target 2920 may be analyzed against hydration status 2923 using a controller 2921 to determine target UFV (per treatment) 2938.

In various embodiments, the controller (e.g., controller 2921) may be, may include, and/or may use a software-based algorithm configured to maintain the hydration status constant or substantially constant, but also to minimize the error (e.g., 2916) between hydration status and hydration target. The output of the controller may be a target UFV (e.g., 2938) for the next PD treatment. The target UFV compensates for changes in hydration status arising from fluid ingestion, urine output (partial kidney function), other insensible losses, and/or the like. The control algorithm may be configured according to various techniques, including, without limitation, a conventional 'PID' (proportional, integral, derivative) controller to more sophisticated expert system approaches.

In the case of PD, the UFV target for the next treatment appropriate values of the dose variables for a sequence of PD cycles. The dose variable values are identified by application of rules, that are encapsulated within an 'inference engine' (e.g., 2901). The rules decide how the dose variables are manipulated most efficiently. Rules may, for example, seek to adjust only dwell duration in preference to changing glucose composition, while ensuring that other dialysis KPIs are met, such as adequate small solute clearance. Control of hydration is possible, for example, using adequate knowledge pertaining to the behavior of the dwell profile, obtained from historical measurements or suitable assumptions. For instance, control can be achieved without the need necessarily for the more generalizable method of UFV prediction. Where there are insufficient degrees of freedom with dwell duration alone, glucose and/or fill volume may be also be manipulated. In some embodiments, the direction in which glucose or dwell duration are manipulated and their magnitude, may depend on the quality of historical data, underlying assumptions, and/or the like.

If a model of the system is invoked, in this case the UFV prediction model, relating the dose variables to the expected UFV, then significantly improved performance may be achieved with regards to control of the patient's hydration status. For example, because dose variables cannot be controlled in real time; their values must be determined prior to each PD treatment cycle. Thus, inclusion of UFV prediction in the inference engine mitigates the potential for oscillations in hydration status as well as minimizing the error between hydration status and the hydration target. Consequently, the UFV prediction capability has high utility in deciding the best combination of dose variables, especially where information on dwell characteristics under different conditions is poor or assumptions are doubtful. This reduces the reliance on rules and also enables other KPIs to be more easily fulfilled, including, without limitation:

The combination of dose variables that lead to the lowest concentration of glucose, mitigating the effects on long term glucose exposure;

Ensuring sufficient time to achieve adequate small solute clearance; and/or

Avoiding dwell durations that are too short, running the risk of sodium loading that can occur in the early part of the dwell due to sodium sieving properties of the peritoneal membrane.

In some embodiments, there may be no or substantially no restrictions regarding the administration of the osmotic agent (e.g., glucose). Many PD treatment systems involve the use of bags of differing glucose strength, leading to discreet glucose composition increments. By contrast, a dedicated glucose proportioning system may allow selection of any specific glucose composition within a defined range. The latter approach offers a finer degree of granularity and is useful in situations where there may be restrictions on dwell duration of individual cycles or overall treatment time.

Feedback control according to some embodiments provides better maintenance of hydration status, the potential advantages of which may include, without limitation:

Minimize cardiovascular (CV) risk by maintenance of optimal hydration status;

Elimination of trial and error PD prescriptions;

The enablement of flexible treatments that can adapt to an individual patient's lifestyle, including Quality of Life (QoL) improvement;

Minimizing the need for different bag combinations, simplifying PD treatment;

Minimizing the exposure to the osmotic agent, affording better long-term membrane preservation; and/or Increase technique survival (as a consequence of reduced CV risk, better QoL and better membrane preservation).

UFV predictions according to some embodiments may be used to determine and/or predict peritonitis and/or signs thereof. Peritonitis (infection of the peritoneal membrane arising from several causes) is a common complication of PD therapy. During an infection, large pores in capillary beds open to increase the release of acute phase proteins such as albumin. This effect may be characterized by a change in the peritoneal membrane transport parameters, particularly in regard to increased dissipation of glucose from the peritoneal cavity, which in turn leads to a reduction in the measured UFV.

The predicted UFV may be obtained from various models described in the present disclosure, the parameters of which are continually updated with data from previous treatments, for instance, via a parameter optimization process (e.g., FIG. 29). It is assumed that high UFV prediction accuracy is achieved by selection of an appropriate regression (statistical) model with sufficient inputs, and interactions between terms as required. Alternatively, UFV may be predicted by any other type of model such as a first principles model. A surrogate marker of peritonitis is obtained by comparing the measured and predicted UFV.

FIG. 30 illustrates an exemplary operating environment in accordance with the present disclosure. More specifically, FIG. 30 depicts a process that includes determining a prescription 3002 with dose variables 3003. In some embodiments, the dose variables 3003 may include a fill volume, fill duration, and/or an osmotic agent concentration. The dose variables 3003 may be included in a design experiment 3012. In various embodiments, design experiment 3012 may include a sequence of PD cycles that involve different combinations of dose variables 3003 performed on a patient 3050 via a PD treatment system 3020. A measured UFV 3036 may be determined for each cycle.

In some embodiments, dose variables 3003 (and unknown factors 3014, such as patient information, time of day, activity levels, etc.) may be provided to a UFV prediction model 3040 configured to generate a predicted UFV 3010. In various embodiments, predicted UFV 3010 may be compared with measured UFV 3036 to determine a probability of peritonitis 3070. In general, in some embodiments, probability of peritonitis 3070 may be a function of or otherwise associated with an error between measured UFV 3036 and predicted UFV 3010.

Under normal circumstances (where no peritonitis is present), the error between the measured and predicted UFV may be small. The higher the difference between the measured and predicted UFV, the greater the probability of peritonitis (e.g., 3070). In some embodiments, the rate of change of measured UFV (improving robustness by minimizing false-positive events) may be monitored. As model parameters are update continually at the end of each PD cycle, various embodiments may include monitoring for sudden change (e.g., a change over a threshold value, percentage, and/or the like) in model parameters.

Where an episode of peritonitis is present, the duration of which may span several days or longer, some embodiments may operate to exclude the treatment data normally used to update model parameters. In other embodiments, where a deviation in UFV or model parameters falls below a 'peritonitis probability threshold', then that data may be used to update model parameters.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. An apparatus, comprising:

at least one processor;

a memory coupled to the at least one processor, the memory comprising instructions that, when executed by the at least one processor, cause the at least one processor to:

access prescription information for a peritoneal dialysis (PD) process for a patient; and provide the prescription information as at least one input to at least one computational model to determine a predicted intraperitoneal volume (IPV), wherein the at least one computational model is trained to determine the predicted IPV based on the prescription information and patient information for at least one prior PD process cycle for the patient or a population of patients associated with the patient;

wherein the prescription information includes a dwell time for the PD process and the patient information includes at least a hydration status of the patient, wherein the at least one processor is further caused to:

send a control signal to a controller of a PD machine to operate the PD machine according to the dwell time for the PD process for the patient, wherein the control signal is generated based on the hydration status of the patient, wherein the at least one computational model includes fuzzy logic configured to vary training data used to train the at least one computational model to determine the predicted IPV to minimize fluctuations of the hydration status of the patient around a target range.

2. The apparatus of claim 1, the prescription information comprising a fill volume and osmotic agent information;

wherein the at least one computational model is a machine learning or artificial intelligence model.

3. The apparatus of claim 1, wherein the patient information comprises at least one of activity level and treatment time-of-day.

4. The apparatus of claim 3, the instructions, when executed by the at least one processor, to cause the at least one processor to provide the patient information as the at least one input to the at least one computational model to determine the predicted IPV.

5. The apparatus of claim 1, wherein the controller of the PD machine comprises a proportional-integral-derivative (PID) controller, wherein the PID controller is configured to perform intraperitoneal pressure (IPP) and hydration status measurements on the patient to maintain the hydration status of the patient within the target range.

6. The apparatus of claim 1, wherein the at least one processor is further caused to:

receive a measured IPV during the PD treatment process for the patient;

determine an error value based on a difference between the predicted IPV and the measured IPV; and update a training of the at least one computational model using the error value.

7. The apparatus of claim 1, wherein the at least one computational model is trained to determine a predicted ultrafiltration volume (UFV) based on the at least one input of the prescription information and a measured drain volume for the PD process.

8. The apparatus of claim 7, the instructions, when executed by the at least one processor, to cause the at least one processor to:

receive the measured drain volume for the PD process, and provide the measured drain volume and the prescription information to the at least one computational model to determine the predicted UFV.

9. The apparatus of claim 7, the at least one computational model configured to determine the predicted UFV according to the following regression model:

$$UFV_{Pred}(t)=a+b\cdot[\text{Glu}]+c\cdot T_{dwell}+d\cdot[\text{Glu}]^2+e\cdot[\text{Glu}]\cdot T_{dwell}+f\cdot T_{dwell}^2,$$

where a, b, c, d, e, and f are regression model coefficients specific to the patient;

wherein Glu is a concentration of an osmotic agent and $T_{dwell}$ is a dwell duration.

10. The apparatus of claim 7, the instructions, when executed by the at least one processor, to cause the at least one processor to:

receive a measured UFV for the PD process, determine an error value based on a comparison of the predicted UFV and the measured UFV, and determine a health condition of the patient based on the error value.

11. The apparatus of claim 10, the health condition comprising peritonitis.

12. An apparatus, comprising:

at least one processor; and a memory coupled to the at least one processor, the memory comprising instructions that, when executed by the at least one processor, cause the at least one processor to:

receive prescription dosage information for a peritoneal dialysis (PD) process for a patient;

determine a predicted ultrafiltration volume (UFV) for the patient by processing the prescription dosage information via a trained computational model, wherein the trained computational model is trained based on at least one prior PD process cycle of the patient and a corresponding ultrafiltration volume measurement;

receive a measured UFV for the PD process of the patient;

determine an error value based on a comparison of the predicted UFV and the measured UFV;

determine a treatment recommendation for the patient based on the error value;

determine a hydration status of the patient; and send a control signal to a controller of a PD machine to control a dwell time of the PD process based on the hydration status of the patient, wherein the PD process includes using the PD machine to treat the patient according to the treatment recommendation during the dwell time, wherein the trained computational model includes fuzzy logic configured to vary training data used to train the trained computational model to predict an IPV to minimize fluctuations of the hydration status of the patient around a target range.

13. The apparatus of claim 12, the prescription dosage information comprising a fill volume, a dwell time, and osmotic agent information;

wherein the trained computational model is a machine learning or artificial intelligence model.

14. The apparatus of claim 12, the instructions, when executed by the at least one processor, to cause the at least one processor to:

receive patient information; and determine the predicted UFV using the trained computational model based on the patient information and the prescription dosage information.

15. The apparatus of claim 14, the patient information comprising at least one of time of day, activity level, or fluid intake.

16. The apparatus of claim 12, the instructions, when executed by the at least one processor, to cause the at least one processor to:

determine a health condition of the patient based on the error value.

17. A method, comprising:

receiving prescription dosage information for a peritoneal dialysis (PD) process for a patient; and determining a predicted ultrafiltration volume (UFV) for the patient by processing the prescription dosage information via a trained computational model, wherein the trained computational model is trained based on at least one prior PD process cycle of the patient and a corresponding ultrafiltration volume measurement;

receiving a measured UFV for the PD process of the patient;

determining an error value based on a comparison of the predicted UFV and the measured UFV;

determining a treatment recommendation for the patient based on the error value;

determining a hydration status of the patient; and sending a control signal to a controller of a PD machine to control a dwell time of the PD process based on the hydration status of the patient, wherein the PD process includes using the PD machine to treat the patient according to the treatment recommendation during the dwell time, wherein the trained computational model includes fuzzy logic configured to vary training data used to train the trained computational model to predict an IPV to minimize fluctuations of the hydration status of the patient around a target range.

18. The method of claim 17, comprising determining a health condition of the patient based on the error value;

wherein the trained computational model is a trained machine learning or artificial intelligence model.

19. The method of claim 17, comprising performing a PD treatment on the patient based on the predicted UFV.

20. The method of claim 17, the prescription dosage information comprising a fill volume, a dwell time, and osmotic agent information.

* * * * *